(12) United States Patent
Oota et al.

(10) Patent No.: US 6,287,547 B1
(45) Date of Patent: Sep. 11, 2001

(54) HAIR TREATMENT COMPOSITION

(75) Inventors: Atsushi Oota; Yoshiyuki Wakahara, both of Kyoto; Shin Sato; Masahiro Kasai, both of Tokyo, all of (JP)

(73) Assignee: Sanyo Chemical Industries, Ltd., Kyoto (JP)

( * ) Notice: Subject to any disclaimer, the term of this patent is extended or adjusted under 35 U.S.C. 154(b) by 0 days.

(21) Appl. No.: 09/417,010

(22) Filed: Oct. 12, 1999

(51) Int. Cl.[7] ............................................. A61K 7/08

(52) U.S. Cl. ................................... 424/70.28; 424/70.19; 424/70.27; 424/70.31

(58) Field of Search .............................. 424/70.1, 70.19, 424/70.27, 70.28, 70.31

(56) References Cited

U.S. PATENT DOCUMENTS 5,089,252 * 2/1992 Grollier et al. .

(List continued on next page.)

FOREIGN PATENT DOCUMENTS 0 636 356 A1 * 2/1995 (EP) .
8-208443    8/1996 (JP) .

(List continued on next page.)

OTHER PUBLICATIONS

Remington's Pharmaceutical Sciences (18th Ed., Mack Printing Company, 1990) pp. 1026–1028.*
Cosmetic and Toiletry Formulations (2d Ed., Noyes Publications, 1992) Sections VII and X.*

*Primary Examiner*—Thurman K. Page
*Assistant Examiner*—P. E. McQueeney
(74) *Attorney, Agent, or Firm*—Connolly Hove Lodge & Hutz

(57) ABSTRACT

A hair treatment composition which comprises an aqueous solution or an aqueous dispersion of at least one quatenary ammonium salt (A) represented by the general formula (I), (2) or (3):

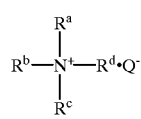

(I)

wherein
$R^a$ represents an organic group containing 6 to 32 carbon atoms,
$R^b$ and $R^c$ are the same or different and each represents an organic group containing 1 to 32 carbon atoms,
$R^d$ represents an organic group containing 1 to 4 carbon atoms, and
$Q^-$ represents an amoni acid anion;

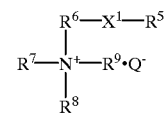

(2)

wherein
$X^1$ represents an ester group;
$R^5$ represents an alkyl, alkenyl or hydroxyalkyl group and $R^6$ represents an alkylene, alkenylene or hydroxyalkylene group, the sum of carbon atoms contained in $R^5$ and $R^6$ being 6 to 32,
$R^7$ and $R^8$ are the same or different and each represents a group of the formula $R^5$—$X^1$—$R^6$—, an alkyl group containing 1 to 4 carbon atoms or a hydroxyalkyl group containing 2 to 4 carbon atoms,
$R^9$ represents an alkyl group containing 1 to 4 carbon atoms or a hydroxyalkyl group containing 2 to 4 carbon atoms, and
$Q^-$ represents an amino acid anion;

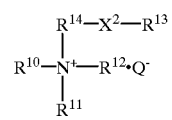

(3)

wherein
$X^2$ represents an amide group,
$R^{13}$ represents an alkyl, alkenyl or hydroxyalkyl group and $R^{14}$ represents an alkylene, alkenylene or hydroxyalkylene group, the sum of carbon atoms contained in $R^{13}$ and $R^{14}$ being 6 to 32,
$R^{10}$ and $R^{11}$ are the same or different and each represents a group of the formula $R^{13}$—$X^2$—$R^{14}$—, a group of the formula $R^5$~$X^1$—$R^6$—, an alkyl group containing 1 to 4 carbon atoms or a hydroxyalkyl group containing 2 to 4 carbon atoms,
$X^1$ represents an ester group, $R^5$ represents an alkyl, alkenyl or hydroxyalkyl group and $R^6$ represents an alkylene, alkenylene or hydroxyalkylene group, the sum of carbon atoms contained in $R^5$ and $R^6$ being 6 to 32,
$R^{12}$ represents an alkyl group containing 1 to 4 carbon atoms or a hydroxyalkyl group containing 2 to 4 carbon atoms, and
$Q^-$ represents an amino acid anion is provided.

20 Claims, No Drawings

U.S. PATENT DOCUMENTS

| | | | |
|---|---|---|---|
| 5,221,794 | * | 6/1993 | Ackerman et al. . |
| 5,234,618 | * | 8/1993 | Kamegai et al. . |
| 5,545,350 | * | 8/1996 | Baker et al. . |
| 5,627,144 | * | 5/1997 | Urfer et al. . |
| 6,004,913 | * | 12/1999 | Iacobucci et al. . |

FOREIGN PATENT DOCUMENTS

| | | | |
|---|---|---|---|
| 9-301936 | | 11/1997 | (JP) . |
| 10-273425 | | 10/1998 | (JP) . |
| 10-273426 | | 10/1998 | (JP) . |
| 99/34768 | * | 7/1999 | (WO) . |

* cited by examiner

HAIR TREATMENT COMPOSITION

FIELD OF THE INVENTION

The present invention relates to a hair treatment composition.

PRIOR ART

The so-far known organic acid quaternary ammonium salts for hair treatment compositions are long-chain alkyl-containing quaternary ammonium salts having a carboxylic acid, a sulfonic acid or a phosphoric acid as the counter ion (JP Kokai Publication H08-208443).

These quaternary ammonium salts, however, cannot be said to be entirely satisfactory in respect of biodegradability, low irritation in humans and performance characteristics (smooth flow of hair, feel after use, typically feel of moistness), although they have been improved as compared with the earlier chloride salts. They have further disadvantages to be overcome; for instance, they fail to increase the product viscosity and are poor in emulsion stability or can hardly be emulsified.

The present inventors made intensive investigations in an attempt to solve those problems and, as a result, found that hair treatment compositions comprising a quaternary ammonium salt of an amino acid, in which the counter ion to the quaternary ammonium is an amino acid anion, are very satisfactory in biodegradability and performance characteristics, insure an increased product viscosity and are excellent in emulsion stability as well. The present invention has been accomplished on the basis of the above findings.

SUMMARY OF THE INVENTION

The present invention is directed to a hair treatment composition which comprises an aqueous solution or an aqueous dispersion of at least one quaternary ammonium salt (A) represented by the general formula (I):

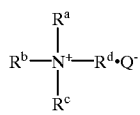

(I)

wherein
- $R^a$ represents an organic group containing 6 to 32 carbon atoms,
- $R^b$ and $R^c$ are the same or different and each represents an organic group containing 1 to 32 carbon atoms,
- $R^d$ represents an organic group containing 1 to 4 carbon atoms and
- $Q^-$ represents an amino acid anion.

As examples of the organic group, there may be mentioned, alkyl, alkenyl, hydroxyalkyl, alkylene, alkenylene, hydroxyalkylene, ester, and amide group, among others.

Preferable quaternary ammonium salts (A) include (A1), (A2) and (A3) as follows.

A quaternary ammonium salt (A1) represented by the general formulas (1)

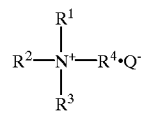

(1)

wherein
- $R^1$ represents an alkyl group containing 6 to 28 carbon atoms, an alkenyl group containing 6 to 28 carbon atoms or a hydroxyalkyl group containing 6 to 28 carbon atoms,
- $R^2$ and $R^3$ are the same or different and each represents an alkyl group containing 1 to 28 carbon atoms, an alkenyl group containing 2 to 28 carbon atoms or a hydroxyalkyl group containing 2 to 28 carbon atoms,
- $R^4$ represents an alkyl group containing 1 to 4 carbon atoms or a hydroxyalkyl group containing 2 to 4 carbon atoms and
- $Q^-$ represents an amino acid anion.

The quaternary ammonium salt (A2) represented by the general formula (2):

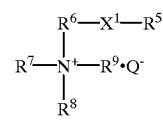

(2)

wherein
- $X^1$ represents an ester group,
- $R^5$ represents an alkyl, alkenyl or hydroxyalkyl group and $R^6$ represents an alkylene, alkenylene or hydroxyalkylene group, the sum of carbon atoms contained in $R^5$ and $R^6$ being 6 to 32,
- $R^7$ and $R^8$ are the same or different and each represents a group of the formula $R^5$—$X^1$—$R^6$— (in which $R^5$, $X^1$ and $R^6$ are as defined above), an alkyl group containing 1 to 4 carbon atoms or a hydroxyalkyl group containing 2 to 4 carbon atoms,
- $R^9$ represents an alkyl group containing 1 to 4 carbon atoms or a hydroxyalkyl group containing 2 to 4 carbon atoms and
- $Q^-$ represents an amino acid anion.

The quaternary ammonium salt (A3) represented by the general formula (3):

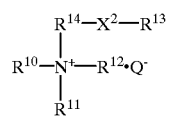

(3)

wherein
- $X^2$ represents an amide group,
- $R^{13}$ represents an alkyl, alkenyl or hydroxyalkyl group and $R^{14}$ represents an alkylene, alkenylene or hydroxyalkylene group, the sum of carbon atoms contained in $R^{13}$ and $R^{14}$ being 6 to 32,
- $R^{10}$ and $R^{11}$ are the same or different and each represents a group of the formula $R^{13}$—$X^2$—$R^{14}$— (in which $R^{13}$, $X^2$ and $R^{14}$ are as defined above), a group of the formula $R^5$—$X^1$—$R^6$— (in which $X^1$ represents an ester group, $R^5$ represents an alkyl, alkenyl or hydroxyalkyl group and $R^6$ represents an alkylene, alkenylene or hydroxyalkylene group, the sum of carbon atoms contained in $R^5$ and $R^6$ being 6 to 32), an alkyl group containing 1 to 4 carbon atoms or a hydroxyalkyl group containing 2 to 4 carbon atoms, $R^{12}$ represents an alkyl group containing 1 to 4 carbon atoms or a hydroxyalkyl group containing 2 to 4 carbon atoms and $Q^-$ represents an amino acid anion.

In the following, the present invention is described in detail.

DETAILED DESCRIPTION OF THE INVENTION

The hair treatment composition of the present invention comprises the quaternary ammonium amino acid salt (A) as essential component.

The quaternary ammonium amino acid salt (A1) to be used in the hair treatment composition of the present invention is represented by the above general formula (1).

In said general formula (1), $R^1$ represents an alkyl group containing 6 to 28 carbon atoms, an alkenyl group containing 6 to 28 carbon atoms or a hydroxyalkyl group containing 6 to 28 carbon atoms. As examples of such group, there may be mentioned, among others, hexyl, heptyl, octyl, nonyl, dodecyl, tetradecyl, hexadecyl, octadecyl, docosyl, 2-ethylhexyl, 2-hexyldecyl, 2-octylundecyl, hexenyl, heptenyl, octenyl, nonenyl, decenyl, dodecenyl, tetradecenyl, hexadecenyl, octadecenyl and hydroxyoctadecyl. If the number of carbon atoms in such group is 5 or less, the feel of hair will be poor and the irritation to skin or the like tends to increase. If such group contains 29 or more carbon atoms, the emulsifiability may be poor in some instances. Among such groups as mentioned above, those groups containing 12 to 24 carbon atoms are preferred and those groups containing 16 to 24 carbon atoms are more preferred because they can provide hair with a moist feel.

In the above general formula (1), $R^2$ and $R^3$ are the same or different and each is an alkyl group containing 1 to 28 carbon atoms, an alkenyl group containing 2 to 28 carbon atoms or a hydroxyalkyl group containing 2 to 28 carbon atoms. As examples of such group, there may be mentioned, among others, methyl, ethyl, propyl, butyl, amyl, hexyl, heptyl, octyl, nonyl, dodecyl, tetradecyl, hexadecyl, octadecyl, docosyl, 2-ethylhexyl, 2-hexyldecyl, 2-octylundecyl, ethenyl, propenyl, butenyl, pentenyl, hexenyl, heptenyl, octenyl, nonenyl, decenyl, dodecenyl, tetradecenyl, hexadecenyl, octadecenyl, hydroxyethyl, hydroxypropyl, hydroxybutyl and hydroxyoctadecyl. If such group contains 29 or more carbon atoms, the emulsifiability may be poor in certain instances. Among such groups as mentioned above, those groups containing 1 to 24 carbon atoms are preferred and those alkyl groups containing 1 to 4 carbon atoms or those hydroxyalkyl groups containing 2 to 4 carbon atoms are more preferred because of better feel of hair after use of the composition and/or good emulsifiability at 50° C.

In the above general formula (1), $R^4$ is an alkyl group containing 1 to 4 carbon atoms or a hydroxyalkyl group containing 2 to 4 carbon atoms. As said alkyl group containing 1 to 4 carbon atoms, there may be mentioned, among others, methyl, ethyl, propyl and butyl. As said hydroxyalkyl group containing 2 to 4 carbon atoms, there may be mentioned, for example, hydroxyethyl, hydroxypropyl and hydroxybutyl. Among them, methyl, ethyl and hydroxyethyl are preferred from the cost viewpoint.

The quaternary ammonium amino acid salt (A1) mentioned above is constituted of the quaternary ammonium (a1) represented by the general formula derived from the above general formula (1) by removing the counter ion $Q^-$, and the amino acid anion represented by $Q^-$. The quaternary ammonium (a1) may be any one represented by said general formula derived from the general formula (1) by removal of the counter ion $Q^-$ and specifically includes, for example, those combinations of $R^1$ to $R^4$ which are shown below in Table 1 under (1) to (15).

TABLE 1

| No. | $R^1$ | $R^2$ | $R^3$ | $R^4$ |
|---|---|---|---|---|
| (1) | $C_8H_7$ | $CH_3$ | $CH_3$ | $C_2H_4$ |
| (2) | $C_{12}H_{25}$ | $CH_3$ | $CH_3$ | $C_2H_4$ |
| (3) | $C_{16}H_{33}$ | $CH_3$ | $CH_3$ | $CH_3$ |
| (4) | $C_{18}H_{37}$ | $CH_3$ | $CH_3$ | $CH_3$ |
| (5) | $C_{22}H_{45}$ | $CH_3$ | $CH_3$ | $CH_3$ |
| (6) | $C_{16}H_{33}$ | $C_{16}H_{33}$ | $CH_3$ | $CH_3$ |
| (7) | $C_{18}H_{37}$ | $C_{18}H_{37}$ | $CH_3$ | $CH_3$ |
| (8) | $C_{22}H_{45}$ | $C_{22}H_{45}$ | $CH_3$ | $CH_3$ |
| (9) | $C_{12}H_{25}$ | $C_{12}H_{25}$ | $C_{12}H_{25}$ | $CH_3$ |
| (10) | $C_{18}H_{37}$ | $C_{18}H_{37}$ | $C_{18}H_{37}$ | $CH_3$ |
| (11) | $C_{22}H_{45\,(85\%)}$ + $C_{18}H_{37\,(15\%)}$ mixed group | $CH_3$ | $CH_3$ | $CH_3$ |
| (12) | coconut alkyl group | $CH_3$ | $CH_3$ | $CH_3$ |
| (13) | beef tallow alkyl group | $CH_3$ | $CH_3$ | $CH_3$ |
| (14) | hardened beef tallow alkyl group | $CH_3$ | $CH_3$ | $CH_3$ |
| (15) | soybean alkyl group | $CH_3$ | $CH_3$ | $CH_3$ |

The amino acid anion, which is the counter ion in the above-mentioned quaternary ammonium amino acid salt (A1), may be the anion of such an amino acid as glycine, alanine, valine, leucine, isoleucine, serine, threonine, cysteine, methionine, asparagine, glutamine, phenylalanine, tyrosine, proline, tryptophan, aspartic acid, glutamic acid, cysteic acid, lysine, arginine or histidine.

The glycine, alanine, valine, leucine, isoleucine, aspartic acid, glutamic acid and cysteic acid anions are preferred among others.

From the viewpoint of cost and ease of salt exchange reaction, in particular, aspartic acid and glutamic acid, which are acidic amino acids, are more preferred. The amino acids mentioned above may be used either singly or as a mixture of two or more.

The quaternary ammonium amino acid salt (A2) to be used in the hair treatment composition of the present invention is represented by the general formula (2) shown above.

In the above general formula (2), $X^1$ is an ester group. Said ester group may be represented by —COO— or —OCO—.

In the above general formula (2), $R^5$ is an alkyl, alkenyl or hydroxyalkyl group. These may be the residues derived from higher fatty acids by removal of the carboxyl group or the residues derived from higher alcohols by removal of the hydroxyl group.

Said higher fatty acids and higher alcohols are not particularly restricted provided that the condition imposed concerning the sum of carbon atoms contained in $R^5$ and $R^6$ as further mentioned later herein is met. Generally they contain 6 to 28 carbon atoms, preferably 12 to 24 carbon atoms. If the number of carbon atoms is 5 or less, the feel of hair will become poor and the irritation to skin may become high in some instances. If the number of carbon atoms is 29 or more, the emulsifiability may be poor in certain instances. Those containing 16 to 24 carbon atoms are preferred among them, since they can provide hair with feel of moistness.

As said higher fatty acids, there may be mentioned, for example, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, behenic acid, oleic acid, linolic acid, linolenic acid and the like. Also useful are mixtures of these, such as coconut oil fatty acids, palm kernel oil fatty acids, beef tallow fatty acids, hardened beef tallow fatty acids, lanolin fatty acids, soybean oil fatty acids and the like.

The higher alcohols mentioned above include, among others, octyl alcohol, decyl alcohol, lauryl alcohol, myristyl alcohol, cetyl alcohol, stearyl alcohol, behenyl alcohol and oleyl alcohol.

mentioned methyl, ethyl, propyl, butyl, hydroxyethyl, hydroxypropyl and hydroxybutyl, among others. Among these, methyl, ethyl and hydroxyethyl are preferred from the cost viewpoint.

The quaternary ammonium amino acid salt (A2) mentioned above is constituted of the quaternary ammonium (a2) represented by the general formula derived from the above general formula (2) by removing the counter ion $Q^-$, and the amino acid anion represented by $Q^-$. The quaternary ammonium (a2) may be any one represented by said general formula derived from the general formula (2) by removal of the counter ion $Q^-$ and specifically includes, for example, those combinations of $R^5$ to $R^9$ and $X^1$ which are shown below in Table 2 and Table 3 under (16) to (31).

TABLE 2

| No | $R^5$ | $X^1$ | $R^6$ | $R^7$ | $R^8$ | $R^9$ |
|---|---|---|---|---|---|---|
| (16) | $C_7H_{15}$ | COO | $(CH_2)_2$ | $HOC_2H_4$ | $CH_3$ | $CH_3$ |
| (17) | $C_{11}H_{23}$ | COO | $(CH_2)_2$ | $HOC_2H_4$ | $HOC_2H_4$ | $CH_3$ |
| (18) | $C_{15}H_{31}$ | COO | $(CH_2)_2$ | $CH_3$ | $CH_3$ | $C_2H_4$ |
| (19) | $C_{17}H_{35}$ | COO | $(CH_2)_2$ | $CH_3$ | $CH_3$ | $CH_3$ |
| (20) | $C_{21}H_{43}$ | COO | $(CH_2)_2$ | $CH_3$ | $CH_3$ | $CH_3$ |
| (21) | $C_{11}H_{23}$ | COO | $(CH_2)_2$ | $C_{11}H_{23}COO(CH_2)_2$ | $CH_3$ | $C_2H_4$ |
| (22) | $C_{17}H_{35}$ | COO | $(CH_2)_2$ | $C_{17}H_{35}COO(CH_2)_2$ | $CH_3$ | $CH_3$ |
| (23) | $C_{11}H_{23}$ | COO | $(CH_2)_2$ | $C_{11}H_{23}COO(CH_2)_2$ | $C_{11}H_{23}COO(CH_2)_2$ | $CH_3$ |
| (24) | $C_{17}H_{35}$ | OCO | $CH_2$ | $C_{17}H_{35}OCOCH_2$ | $CH_3$ | $CH_3$ |
| (25) | $C_{21}H_{43}$ | OCO | $CH_2$ | $CH_3$ | $CH_3$ | $C_2H_4$ |

In the above general formula (2), $R^6$ is an alkylene, alkenylene or hydroxyalkylene group. These are not particularly restricted provided that the condition imposed concerning the sum of carbon atoms contained in $R^5$ and $R^6$ as mentioned later herein is met. Generally, however, they contain 1 to 4 carbon atoms. Examples are methylene, ethylene, propylene, butylene, hydroxyethylene, hydroxypropylene and hydroxybutylene, among others. Among these, methylene, ethylene and propylene are preferred from the cost viewpoint.

In the above general formula (2), the sum of carbon atoms contained in $R^5$ and $R^6$ is 6 to 32. When the sum of carbon atoms is less than 6, the feed of hair will become poor and the irritation to skin may become high in certain instances. If it exceeds 32, the emulsifiability may become poor in some instances. The sum of carbon atoms is preferably 16 to 28, since hair can be provided with feel of moistness in that case.

In the above general formula (2), $R^7$ and $R^8$ are the same or different and each is a group of the formula $R^5$—$X^1$—$R^6$—, an alkyl group containing 1 to 4 carbon atoms or a hydroxyalkyl group containing 2 to 4 carbon atoms. Preferred are alkyl groups containing 1 to 4 carbon atoms or hydroxyalkyl groups containing 2 to 4 carbon atoms.

In the above-mentioned group $R^5$—$X^1$—$R^6$—, $X^1$, $R^5$ and $R^6$ are as mentioned hereinabove.

The above-mentioned alkyl group containing 1 to 4 carbon atoms is, for example, methyl, ethyl, propyl or butyl. The above-mentioned hydroxyalkyl group containing 2 to 4 carbon atoms is, for example, hydroxyethyl, hydroxypropyl or hydroxybutyl.

In the above general formula (2), $R^9$ is an alkyl group containing 1 to 4 carbon atoms or a hydroxyalkyl group containing 2 to 4 carbon atoms. Specifically, there may be

TABLE 3

| No. | $R^5$ | $X^1$ | $R^6$ | $R^7$ | $R^8$ | $R^9$ |
|---|---|---|---|---|---|---|
| (26) | $C_{21}H_{43}$ (85%) + $C_{17}H_{35}$ (15%) mixed group | COO | $(CH_2)_2$ | $CH_3$ | $CH_3$ | $CH_3$ |
| (27) | coconut oil fatty acid residue | COO | $(CH_2)_2$ | $CH_3$ | $CH_3$ | $CH_3$ |
| (28) | palm kernel oil fatty acid residue | COO | $(CH_2)_2$ | $CH_3$ | $CH_3$ | $CH_3$ |
| (29) | beef tallow fatty acid residue | COO | $(CH_2)_2$ | $CH_3$ | $CH_3$ | $CH_3$ |
| (30) | hardened beef tallow fatty acid residue | COO | $(CH_2)_2$ | $CH_3$ | $CH_3$ | $CH_3$ |
| (31) | lanolin fatty acid residue | COO | $(CH_2)_2$ | $CH_3$ | $CH_3$ | $CH_3$ |

Suited for use as the amino acid anion, which is the counter ion in the above-mentioned quaternary ammonium amino acid salt (A2), are those specifically mentioned hereinabove in relation to the quaternary ammonium amino acid salt (A1).

The quaternary ammonium amino acid salt (A3) to be used in the hair treatment composition of the present invention is represented by the general formula (3) shown above.

In the above general formula (3), $X^2$ is an amide group. Said amide group may be represented by —CONH— or —NHCO—.

In the above general formula (3), $R^{13}$ is an alkyl, alkenyl or hydroxyalkyl group. These may be the residues derived from higher fatty acids by removal of the carboxyl group or the residues derived from primary amines by removal of the amino group.

Said higher fatty acids and primary amines are not particularly restricted provided that the condition imposed concerning the sum of carbon atoms contained in $R^{13}$ and $R^{14}$ as mentioned later herein is met. Generally they contain 6 to 28 carbon atoms, preferably 12 to 24 carbon atoms. If the number of carbon atoms is 5 or less, the feel of hair will become poor and the irritation to skin may become pronounced in some instances. If the number of carbon atoms is 29 or more, the emulsifiability may become compromised in certain instances. Those containing 16 to 24 carbon atoms are preferred among others, since they can provide hair with a moist feel.

As said higher fatty acids, there may be mentioned, for example, those specifically mentioned hereinabove.

Said primary amines include but are not limited to octylamine, decylamine, laurylamine, myristylamine, cetylamine, stearylamine, behenylamine and oleylamine.

In the above general formula (3), $R^{14}$ is an alkylene, alkenylene or hydroxyalkylene group. These are not particularly restricted provided that the condition imposed concerning the sum of carbon atoms contained in $R^{13}$ and $R^{14}$ as mentioned below is met. Generally, however, they contain 1 to 4 carbon atoms. As examples of such groups, there may be mentioned, among others, methylene, ethylene, propylene, butylene, hydroxyethylene, hydroxypropylene and hydroxybutylene. Among these, methylene, ethylene and propylene are preferred from the viewpoint of cost.

Referring to the above general formula (3), the sum of carbon atoms contained in $R^{13}$ and $R^{14}$ is 6 to 32. If said number of carbon atoms is less than 6, the feel of hair will become poor and the irritation to skin may be high in some instances. It exceeds 32, the emulsifiability will be poor in certain instances. The sum of carbon atoms is preferably 16 to 28, since, in that case, hair can be given feel of moistness.

In the above general formula (3), $R^{10}$ and $R^{11}$ are the same or different and each is a group of the formula $R^{13}$—$X^2$—$R^{14}$—, a group of the formula $R^5$—$X^1$—$R^6$—, an alkyl group containing 1 to 4 carbon atoms or a hydroxyalkyl group containing 2 to 4 carbon atoms, preferably an alkyl group containing 1 to 4 carbon atoms or a hydroxyalkyl group containing 2 to 4 carbon atoms.

In said group $R^{13}$—$X^2$—$R^{14}$—, $R^{13}$, $X^2$ and $R^{14}$ are as mentioned above. Those containing 16 to 28 carbon atoms are preferred among others, since they can give feel of moistness to hair.

In said group $R^5$—$X^1$—$R^6$—, $R^5$, $X^1$ and $R^6$ are as mentioned above. Those containing 16 to 28 carbon atoms are preferred among others, since they can give feel of moistness to hair.

As the alkyl group containing 1 to 4 carbon atoms or the hydroxyalkyl group containing 2 to 4 carbon atoms mentioned above, there may be mentioned, for example, methyl, ethyl, propyl, butyl, hydroxyethyl, hydroxypropyl and hydroxybutyl.

In the above general formula (3), $R^{12}$ is an alkyl group containing 1 to 4 carbon atoms or a hydroxyalkyl group containing 2 to 4 carbon atoms. As examples of such groups, there may be mentioned methyl, ethyl, propyl, butyl, hydroxyethyl, hydroxypropyl and hydroxybutyl, among others. From the viewpoint of cost, methyl, ethyl and hydroxyethyl are particularly preferred.

The quaternary ammonium amino acid salt (A3) mentioned above is constituted of the quaternary ammonium (a3) represented by the general formula derived from the above general formula (3) by removal of the counter ion $Q^-$, and the amino acid anion represented by $Q^-$. Said quaternary ammonium (a3) may be any one represented by the general formula derived from the above general formula (3) by removal of the counter ion $Q^-$ and typically includes, for example, those combinations of $R^{10}$ to $R^{14}$ and $X^2$ which are shown below in Table 4 and Table 5 under (32) to (47).

TABLE 4

| No. | $R^{13}$ | $X^2$ | $R^{14}$ | $R^{10}$ | $R^{11}$ | $R^{12}$ |
|---|---|---|---|---|---|---|
| (32) | $C_{11}H_{23}$ | CONH | $(CH_2)_3$ | $CH_3$ | $CH_3$ | $CH_3$ |
| (33) | $C_{17}H_{35}$ | CONH | $(CH_2)_3$ | $CH_3$ | $CH_3$ | $CH_3$ |
| (34) | $C_{21}H_{43}$ | CONH | $(CH_2)_3$ | $CH_3$ | $CH_3$ | $CH_3$ |
| (35) | $C_{11}H_{23}$ | CONH | $(CH_2)_3$ | $C_{11}H_{23}CONH(CH_2)_3$ | $CH_3$ | $C_2H_4$ |
| (36) | $C_{17}H_{35}$ | CONH | $(CH_2)_3$ | $C_{17}H_{35}CONH(CH_2)_3$ | $CH_3$ | $CH_3$ |
| (37) | $C_{11}H_{23}$ | CONH | $(CH_2)_3$ | $C_{11}H_{23}CONH(CH_2)_3$ | $C_{11}H_{23}CONH(CH_2)_3$ | $CH_3$ |
| (38) | $C_{17}H_{35}$ | NHCO | $CH_2$ | $C_{17}H_{35}NHCOCH_2$ | $CH_3$ | $CH_3$ |
| (39) | $C_{21}H_{43}$ | NHCO | $CH_2$ | $CH_3$ | $CH_3$ | $CH_3$ |
| (40) | $C_{21}H_{43}$ | CONH | $(CH_2)_3$ | $C_{21}H_{43}COO(CH_2)_2$ | $CH_3$ | $CH_3$ |
| (41) | $C_{21}H_{43}$ | NHCO | $CH_2$ | $C_{21}H_{43}OCOCH_2$ | $CH_3$ | $CH_3$ |

TABLE 5

| No. | $R^{13}$ | $X^2$ | $R^{14}$ | $R^{10}$ | $R^{11}$ | $R^{12}$ |
|---|---|---|---|---|---|---|
| (42) | $C_{21}H_{43}$ (85%) + $C_{17}H_{35}$ (15%) mixed group | CONH CONH | $(CH_2)_3$ | $CH_3$ | $CH_3$ | $CH_3$ |
| (43) | coconut oil fatty acid residue | CONH | $CH_2)_3$ | $CH_3$ | $CH_3$ | $CH_3$ |
| (44) | palm kernel oil fatty acid residue | CONH | $CH_2)_3$ | $CH_3$ | $CH_3$ | $CH_3$ |
| (45) | beef tallow fatty acid residue | CONH | $CH_2)_3$ | $CH_3$ | $CH_3$ | $CH_3$ |
| (46) | hardened beef tallow fatty acid residue | CONH | $CH_2)_3$ | $CH_3$ | $CH_3$ | $CH_3$ |
| (47) | lanolin fatty acid residue | CONH | $CH_2)_3$ | $CH_3$ | $CH_3$ | $CH_3$ |

Suited for use as the amino acid anion, which is the counter ion in the above-mentioned quaternary ammonium amino acid salt (A3), are those specifically given hereinabove as examples of the amino acid anion in the quaternary ammonium amino acid salt (A1).

It is preferred that the hair treatment composition of the present invention which comprises the quaternary ammonium amino acid salt (A) further contains at least one tertiary amine salt (B) represented by the general formula (4):

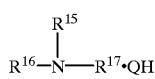

(4)

In the above formula, $R^{15}$ represents an alkyl group containing 6 to 28 carbon atoms, an alkenyl group containing 6 to 28 carbon atoms, a hydroxyalkyl group containing 6 to 28 carbon atoms, a group of the formula $R^5$—$X^1$—$R^6$— or a group of the formula $R^{13}$—$X^2$—$R^{14}$—. $R^{16}$ and $R^{17}$ are the same or different and each represents an alkyl group containing 1 to 28 carbon atoms, an alkenyl group containing 2 to 28 carbon atoms, a hydroxyalkyl group containing 2 to 28 carbon atoms, a group of the formula $R^5$—$X^1$—$R^6$— or a group of the formula $R^{13}$—$X^2$—$R^{14}$—. QH represents an amino acid.

In the above general formula (4), which represents the tertiary amine salt (B), $R^{15}$ is an alkyl group containing 6 to 28 carbon atoms, an alkenyl group containing 6 to 28 carbon atoms, a hydroxyalkyl group containing 6 to 28 carbon atoms, a group of the formula $R^5$—$X^1$—$R^6$— or a group of the formula $R^{13}$—$X^2$—$R^{14}$—.

As said alkyl group containing 6 to 28 carbon atoms, said alkenyl group containing 6 to 28 carbon atoms or said hydroxyalkyl group containing 6 to 28 carbon atoms, there may be mentioned, for example, those respectively mentioned specifically hereinabove. Those groups containing 12 to 24 carbon atoms are preferred among others.

Referring to the group $R^5$—$X^1$—$R^6$—, $X^1$, $R^5$ and $R^6$ may be the same as those mentioned hereinabove.

Referring to the group $R^{13}$—$X^2$—$R^{14}$—, $X^2$, $R^{13}$ and $R^{14}$ may be the same as those mentioned hereinabove.

In the above general formula (4), $R^{16}$ and $R^{17}$ are the same or different and each is an alkyl group containing 1 to 28 carbon atoms, an alkenyl group containing 2 to 28 carbon atoms, a hydroxyalkyl group containing 2 to 28 carbon atoms, a group of the formula $R^5$—$X^1$—$R^6$— or a group of the formula $R^{13}$—$X^2$—$R^{14}$—.

As said alkyl group containing 1 to 28 carbon atoms, said alkenyl group containing 2 to 28 carbon atoms or said hydroxyalkyl group containing 2 to 28 carbon atoms, there may be mentioned, for example, those respectively mentioned hereinabove as examples of such. If the number of carbon atoms is above 29, the emulsifiability may be poor in some instances. Among those groups, the groups containing 1 to 24 carbon atoms are preferred and, further, from the viewpoint of feel of hair after use or emulsion stability at 50° C., those alkyl groups which contain 1 to 4 carbon atoms and those hydroxyalkyl groups which contain 2 to 4 carbon atoms are more preferred.

Said tertiary amine salt (B) is constituted of the tertiary amine (b) represented by the general formula derived from the above general formula (4) by removal of the amino acid QH, and the amino acid represented by QH. Said tertiary amine (b) may be any one represented by said general formula derived from the general formula (4) by removal of the amino acid QF and typically includes, for example, those combinations of $R^{15}$ to $R^{17}$ which are shown below in Tables 6 to 8 under (101) to (139).

TABLE 6

| No. | $R^{15}$ | $R^{16}$ | $R^{17}$ |
| --- | --- | --- | --- |
| 101 | $C_8H_{17}$ | $CH_3$ | $CH_3$ |
| 102 | $C_{12}H_{25}$ | $CH_3$ | $CH_3$ |
| 103 | $C_{16}H_{33}$ | $CH_3$ | $CH_3$ |
| 104 | $C_{18}H_{37}$ | $CH_3$ | $CH_3$ |
| 105 | $C_{22}H_{45}$ | $CH_3$ | $CH_3$ |
| 106 | $C_{16}H_{33}$ | $C_{16}H_{33}$ | $CH_3$ |
| 107 | $C_{18}H_{37}$ | $C_{18}H_{37}$ | $CH_3$ |
| 108 | $C_{22}H_{45}$ | $C_{22}H_{45}$ | $CH_3$ |
| 109 | $C_{12}H_{25}$ | $C_{12}H_{25}$ | $C_{12}H_{25}$ |
| 110 | $C_{18}H_{37}$ | $C_{18}H_{37}$ | $C_{18}H_{37}$ |
| 111 | $C_{21}H_{43}(85\%)$ + $C_{17}H_{35(15\%)}$ mixed group | $CH_3$ | $CH_3$ |
| 112 | coconut alkyl group | $CH_3$ | $CH_3$ |
| 113 | beef tallow alkyl group | $CH_3$ | $CH_3$ |
| 114 | hardened beef tallow alkyl group | $CH_3$ | $CH_3$ |
| 115 | soybean alkyl group | $CH_3$ | $CH_3$ |

TABLE 7

| No. | $R^{15}$ | $R^{16}$ | $R^{17}$ |
| --- | --- | --- | --- |
| 116 | $C_7H_{15}COO(CH_2)_2$ | $HOC_2H_4$ | $CH_3$ |
| 117 | $C_{11}H_{23}COO(CH_2)_2$ | $HOC_2H_4$ | $HOC_2H_4$ |
| 118 | $C_{15}H_{31}COO(CH_2)_2$ | $CH_3$ | $CH_3$ |
| 119 | $C_{17}H_{35}COO(CH_2)_2$ | $CH_3$ | $CH_3$ |
| 120 | $C_{21}H_{43}COO(CH_2)_2$ | $CH_3$ | $CH_3$ |
| 121 | $C_{11}H_{23}COO(CH_2)_2$ | $C_{11}H_{23}COO(CH_2)_2$ | $CH_3$ |
| 122 | $C_{17}H_{35}COO(CH_2)_2$ | $C_{17}H_{35}COO(CH_2)_2$ | $CH_3$ |
| 123 | $C_{11}H_{23}COO(CH_2)_2$ | $C_{11}H_{23}COO(CH_2)_2$ | $C_{11}H_{23}COO(CH_2)_2$ |
| 124 | $C_{11}H_{23}CONHCH_2)_3$ | $CH_3$ | $CH_3$ |
| 125 | $C_{17}H_{35}CONHCH_2)_3$ | $CH_3$ | $CH_3$ |
| 126 | $C_{21}H_{43}CONHCH_2)_3$ | $CH_3$ | $CH_3$ |
| 127 | $C_{11}H_{23}CONHCH_2)_3$ | $C_{11}H_{23}CONH(CH_2)$ | $CH_3$ |
| 128 | $C_{17}H_{35}CONHCH_2)_3$ | $C_{17}H_{35}CONH(CH_2)$ | $CH_3$ |
| 129 | $C_{11}H_{23}CONHCH_2)_3$ | $C_{11}H_{23}CONH(CH_2)$ | $C_{11}H_{23}CONHCH_2)_3$ |
| 130 | $C_{17}H_{35}OCOCH_2$ | $C_{17}H_{35}OCOCH_2$ | $CH_3$ |
| 131 | $C_{21}H_{43}OCOCH_2$ | $CH_3$ | $CH_3$ |
| 132 | $C_{17}H_{35}NHCOCH_2$ | $C_{17}H_{35}NHCOCH_2$ | $CH_3$ |
| 133 | $C_{21}H_{43}NHCOCH_2$ | $CH_3$ | $CH_3$ |
| 134 | $C_{21}H_{43}COO(CH_2)_2$ | $C_{21}H_{43}CONHCH_2)_3$ | $CH_3$ |
| 135 | $C_{21}H_{43}OCOCH_2$ | $C_{21}H_{43}NHCOCH_2$ | $CH_3$ |

TABLE 8

| No. | $R^{15}$ | $R^{16}$ | $R^{17}$ |
| --- | --- | --- | --- |
| 136 | $C_{21}H_{43}COO(CH_2)_2(85\%)$ + $C_{17}H_{35}COO(CH_2)_2(15\%)$ mixed group | $CH_3$ | $CH_3$ |
| 137 | $C_{21}H_{43}CONH(CH_2)_3(85\%)$ + $C_{17}H_{35}CONH(CH_2)_3(15\%)$ mixed group | $CH_3$ | $CH_3$ |
| 138 | hardened beef tallow fatty acid residue + $COO(CH_2)_2$ | $CH_3$ | $CH_3$ |
| 139 | hardened beef tallow fatty acid residue + $CONH(CH_2)_3$ | $CH_3$ | $CH_3$ |

Suited for use as the amino acid which constitutes the above-mentioned tertiary amine salt (B) are those amino acids specifically mentioned hereinabove as examples of the amino acid anion constituting the quaternary ammonium amino acid salt (A1).

The quaternary ammonium amino acid salt (A1) can be produced generally by quaternizing the corresponding tertiary amine with an alkylating agent such as an alkyl halide (e.g. methyl chloride), a dialkyl sulfate (e.g. dimethyl sulfate) or a dialkyl carbonate (e.g. dimethyl carbonate) and then subjecting the resulting quaternary ammonium salt to salt exchange with an amino acid or a salt thereof. From the viewpoint of freeness from inorganic salt formation and good emulsion stability, among others, it is particularly preferable to produce said salt (A1) by quaternization with a dialkyl carbonate, such as dimethyl carbonate, followed by salt exchange with an amino acid.

When a dialkyl carbonate is used as the alkylating agent in the quaternization reaction mentioned above, it is used generally in an amount of 0.5 to 5.0 moles, preferably 0.7 to 2.0 moles, per mole of the tertiary amine.

Said quaternization reaction is generally carried out at a temperature of 50 to 150° C., preferably 80 to 120° C. At a temperature below 50° C., the reaction rate will be very slow and the product may possibly solidify, which will make stirring impossible. At a temperature above 150° C., intense discoloration will occur.

In said salt exchange with the amino acid, the amino acid is used generally in an amount of 0.5 to 3.0 moles, preferably 0.5 to 2.0 moles, per mole of the intermediate quaternary ammonium salt.

Said salt exchange with the amino acid is carried out generally at a temperature of 50 to 150° C., preferably 70 to 120° C. At a temperature below 50° C., solidification may occur, making stirring impossible and, at a temperature above 150° C., intense discoloration will occur.

The quaternary ammonium amino acid salt (A2) mentioned above can be produced by first preparing a tertiary amine having the group $R^5-X^1-R^6-$ and then following such a procedure for producing the quaternary ammonium amino acid salt as mentioned above.

Said $R^5-X^1-R^6-$ group-containing tertiary amine can be prepared generally by subjecting an alkylamino alcohol, such as dimethylaminoethanol, and carboxylic acid, such as behenic acid, to dehydration condensation for esterification in the presence of a catalyst, such as p-toluenesulfonic acid or potassium hydroxide.

In the above esterification reaction, the alkylamino alcohol is used generally in an amount of 0.1 to 5.0, preferably 0.3 to 3.0 moles, per mole of the carboxylic acid.

Said esterification reaction is carried out generally at a temperature of 100 to 220° C., preferably 120 to 180° C. At a temperature below 100° C., the reaction rate is very slow and, at above 220° C., intense discoloration will occur.

The quaternary ammonium amino acid salt (A3) mentioned above can be produced generally by first preparing a tertiary amine having the group $R^{13}-X^2-R^{14}-$ and then following such a procedure for producing the quaternary ammonium amino acid salt as mentioned above.

Said $R^{13}-X^2-R^{14}-$ group-containing tertiary amine can be prepared generally by subjecting an alkylaminoalkyleneamine, such as dimethylaminopropylamine, and a carboxylic acid, such as behenic acid, to dehydration condensation for amidation.

In the above amidation reaction, the alkylaminoalkyleneamine is used generally in an amount of 0.1 to 5.0 moles, preferably 0.3 to 3.0 moles, per mole of the carboxylic acid.

Said amidation reaction is carried out generally at a temperature of 100 to 220° C., preferably 120 to 180° C. At a temperature below 100° C., the reaction rate is very slow and, at above 220° C., intense discoloration will occur.

The tertiary amine salt (B) mentioned above can be produced by neutralizing the corresponding tertiary amine with an amino acid.

In the neutralization reaction, the amino acid is used generally in an amount of 0.5 to 3.0 moles, preferably 0.5 to 2.0 moles, per mole of the tertiary amine.

The neutralization reaction is generally carried out at a temperature of 50 to 150° C., preferably 70 to 120° C. At a temperature below 50° C., solidification may occur to interfere with stirring. If 150° C. is exceeded, intense discoloration will occur.

The quaternary ammonium salt (A), even when used singly, expresses its performance characteristics such as biodegradability, low irritation to humans and good feel in and after use (posttreatment feel of hair, typically smooth flow of hair and feel of moistness) to a satisfactory extent. When the above-mentioned salt (A) is used in combination with the tertiary amine salt (B) mentioned above, however, the product viscosity of the hair treatment composition can be further increased and, furthermore, the emulsion stability can be further improved. In this case, the weight ratio (A)/(B) is generally 99.9/0.1 to 50/50, preferably 99.9/0.1 to 70/30. If the proportion of (A) is less than 50% by weight, the posttreatment feel of hair, typically the smooth flow and moist feel of hair, will become poor.

In the hair treatment composition of the present invention, the proportion of the quaternary ammonium salt (A) or of the mixture of said salt (A) plus the tertiary amine salt (B) is generally 0.1 to 30% by weight, preferably 0.5 to 20% by weight, based on the final hair treatment composition. If the proportion is less than 0.1% by weight, the posttreatment feel of hair, typically the smooth flow and moist feel of hair, may be poor in certain instances. If it exceeds 30% by weight, gelation tends to occur.

As for the field of use, the hair treatment composition of the present invention is applicable to every field in which the conventional quaternary ammonium salt-containing hair treatment compositions have been used. In particular, it is useful as a hair rinse, hair conditioner, hair treatment, shampoo, hair dye, and mousse or like hair setting composition, among others.

For use as a hair rinse, conditioner or treatment, the hair treatment composition of the present invention generally comprises the quaternary ammonium salt (A) and optionally the tertiary amine salt (B) and may further contain a nonionic surfactant, oil, humectant, chelating agent, lower alcohol, racromolecular compound, perfume, colorant, preservative, ultraviolet absorber, etc.

Said nonionic surfactant includes, among others, 1:1 type coco fatty acid diethanolamide, lauryldimethylamine oxide, glycerol monostearate, ethylene glycol monostearate, polyethylene glycol monostearate, polyethylene glycol distearate, sorbitan monolaurate, polyoxyethylene-sorbitan monolaurate, polyoxyethylene dioleate, methyl glucoside, polyoxyethylene-beef tallow alkyl hydroxymyristylene ether, ethylene glycol distearate and the like. Among them, glycerol monostearate and ethylene glycol monostearate are preferred because they afford good emulsion stability at 50° C.

Said oil includes, among others, higher alcohols such as cetyl alcohol, stearyl alcohol and behenyl alcohol; fatty acid esters such as octyl myristate, cetyl 2-ethylhexanoate, isopropyl myristate and cetyl palmitate; hydrocarbon compounds such as solid paraffin, liquid paraffin and squalane; silicones such as dimethylpolysiloxane, modified silicones derived from dimethylpolysiloxane by introduction of various organic groups in lieu of some methyl groups, and cyclic dimethylpolysiloxane; and the like. Among them, higher alcohols and silicones are preferred because of their ability to provide hair with feel of moistness.

Said humectant includes, among others, glycerol, diglycerol and sodium pyrrolidonecarboxylate. From the cost viewpoint, glycerol is particularly preferred.

Said chelating agent includes, among others, ethylenediaminetetraacetic acid sodium salt, 1-hydroxyethane-1,1-diphosphonic acid sodium salt and the like. These may be used according to need.

Said lower alcohol includes, among others, ethanol, propylene glycol and dipropylene glycol. These may be used according to need.

Said macromolecular compound includes, among others, cationized cellulose, canionized guar gum, polyethylene glycol, polypropylene glycol, sodium polyacrylate, hydroxyethylcellulose, protein derivatives, (N-methacryloyloxyethyl-N,N-dimethylammonium-α-N-methylcarboxybetaine)-(alkyl methacrylate) copolymers and the like. Among them, cationized cellulose and cationized guar gum are preferred because of their ability to provide hair with moist feel.

For use as a hair rinse, conditioner or treatment, the hair treatment composition of the present invention is formulated generally as follows: 0.5 to 20% by weight of a cationic surfactant comprising said quaternary ammonium salt (A) or a mixture of said salt (A) and the tertiary amine salt (B), 0 to 5% by weight of said nonionic surfactant, 0.5 to 30% by weight of said oil, 0 to 10% by weight of said humectant, 0 to 10% by weight of an additive selected from the group consisting of said chelating agent, lower alcohol, macromolecular compound, perfumes, colorants, preservations and ultraviolet absorbers, and 25 to 99% by weight of water.

From the viewpoint of posttreatment feel of hair, typically smooth flow and moist feel of hair, said oil is used preferably in a proportion of 1/1 to 1/4 by weight relative to the quaternary ammonium salt (A) or the mixture of said (A) and the tertiary amine salt (B).

In addition, an anionic surfactant, amphoteric surfactant, cationic surfactant or the like may be combinedly used within limits within which the effects of the present invention will not be sacrificed.

Said anionic surfactant includes, among others, sodium lauryl sulfate, sodium polyoxyethylene lauryl sulfate, triethanolamine polyoxyethylene lauryl sulfate, sodium polyoxyethylene lauryl ether acetate, sodium polyoxyethylene coco fatty acid monoethanolamide sulfate, disodium polyoxyethylene lauryl sulfosuccinate, sulfosuccinic acid polyoxyethylenelauroylethanolamide disodium, coco fatty acid methyltaurine sodium, coco fatty acid methyltaurine magnesium, coco fatty acid sarcosine sodium, coco fatty acid sarcosine triethanolamine, sodium N-coco fatty acid acyl-L-glutamate, triethanolamine N-coco fatty acid acyl-L-glutamate, lauroylmethyl-β-alanine sodium, N-lauroyl-N-methyl-β-alanine triethianolamine salt, sodium lauryl phosphate and the like.

Said amphoteric surfactant includes, among others, coco fatty acid amidopropyldimethylaminoacetic acid betaine, lauryldimethylaminoacetic acid betaine, 2-alkyl-N-carboxymethyl-N-hydroxyethylimidazolinium betaines, laurylhydroxysulfobetaine, lauroylamidoethylhydroxyethylcarboxymethylbetaine hydroxypropylphosphoric acid sodium salt, sodium β-laurylaminopropionate and the like.

Usable as said cationic surfactant are quaternary ammonium salts other than the quaternary ammonium salt (A), which is to be used in the practice of the present invention. As examples, there may be mentioned, among others, stearyltrimethylammonium chloride, behenyltrimethylammonium chloride, distearyldimethylammonium chloride, lanolin fatty acid-aminopropylethyldimethylammonium ethylsulfate, stearic acid diethylaminoethylamide lactic acid salt, stearic acid dimethylaminopropylamide lactic acid salt and the like. For use as a hair rinse, conditioner or treatment, the composition contains 0.5 to 20% by weight of total cationic surfactants based on the composition.

For use as a shampoo, the hair treatment composition of the present invention comprises the quaternary ammonium salt (A) and optionally the tertiary amine salt (B) and may further contain an anionic surfactant, amphoteric surfactant, nonionic surfactant, humectant, chelating agent, macromoelcular compound, perfume, colorant, preservative, ultraviolet absorber, etc.

Useful as such anionic surfactant, amphoteric surfactant, nonionic surfactant, humectant, chelating agent and macromolecular compound are those respectively mentioned specifically hereinabove.

For use as a shampoo, the hair treatment composition of the present invention is generally formulated as follows: 0.5 to 10% by weight of a cationic surfactant comprising said quaternary ammonium salt (A) or the mixture of said salt (A) and the tertiary amine salt (B), 1.0 to 30% by weight of said anionic surfactant, 0 to 10% by weight of said amphoteric surfactant, 0.5 to 10% by weight of said nonionic surfactant, 0 to 10% by weight of said humectant, 0 to 5% by weight of an additive selected from the group consisting of said chelating agent, macromolecular compound, perfumes, colorants, preservations and ultraviolet absorbers, and 25 to 98% by weight of water.

In addition, a cationic surfactant may be combinedly used within limits within which the effects of the present invention will not be sacrificed. For use as a shampoo, the composition contains 0.5 to 10% by weight of total cationic surfactants based on the composition. Suited for use as such cationic surfactant are, among others, those cationic surfactants specifically mentioned hereinabove.

Where necessary, one or more other additives may be incorporated in the composition. Thus, for example, those oils specifically mentioned hereinabove as well as higher fatty acids such as stearic acid may be used as oils, and trichiorocarbanilide, sulfur, salicylic acid, zinc pyrithione, isopropylmethylphenol or the like may be added as a medicine.

For use as a hair dye, the hair treatment composition of the present invention generally comprises the quaternary ammonium salt (A) and optionally the tertiary amine salt (B) and, in addition, contains an acid dye, solvent, pH adjusting agent, thickener, etc.

Said acid dye is not particularly restricted but may be any one belonging to the class of azo dyes or anthraquinone dyes.

Said solvent includes, among others, benzyl alcohol, isopropyl alcohol and other lower alcohols; N-methylpyrrolidone and the like.

Said pH adjusting agent is, for example, citric acid.

Said thickener includes, among others, carboxymethylcellulose, xanthan gum and the like.

For use as a hair dye, the hair treatment composition of the present invention is formulated as follows: 0.1 to 5% by weight of a cationic surfactant comprising said quaternary ammonium salt (A) or the mixture of said salt (A) and the tertiary amine salt (B), 0.5 to 10% by weight of the acid dye, 1 to 30% by weight of the solvent, 0 to 5% by weight of the pH adjusting agent, 0 to 5% by weight of the thickener, and 45 to 98.4% by weight of water.

In addition, an anionic surfactant, amphoteric surfactant, nonionic surfactant, cationic surfactant and/or the like may be combinedly used within limits within which the effects of the present invention will not be sacrificed. For use as a hair dye, the composition contains 0.1 to 5% by weight of total cationic surfactants based on the composition. Suited for use as such anionic surfactant, amphoteric surfactant, nonionic surfactant and cationic surfactant are, among others, those specifically mentioned hereinabove.

Where necessary, one or more other additives may be incorporated in the composition. Thus, for example, there may be incorporated those oils, humectants, chelating agents and/or macromolecular compounds specifically mentioned hereinabove as well as a perfume, colorant, preservative, ultraviolet absorber, etc.

For use as a hair setting agent, such as mousse, the hair treatment composition of the present invention generally comprises the quaternary ammonium salt (A) and optionally the tertiary amine salt (B) and further contains a macromolecular compound, oil, humectant, chelating agent, lower alcohol, nonionic surfactant, perfume, colorant, preservative, ultraviolet absorber, etc.

In particular when the above composition is used as a hair foam or hair spray, said composition is filled into a can, together with a liquefied petroleum gas, dimethyl ether, etc. By doing so, the can advantageously be prevented from rusting.

Said macromolecular compound includes not only those specifically mentioned hereinabove but also acrylic resin-alkanolamines, carboxyvinyl polymers, polyvinylpyrrolidone-vinyl acetate copolymers and the like.

Said oil includes not only those specifically mentioned hereinabove but also waxes such as refined Japan wax and white beeswax, and so forth.

Suited for use as said humectant, chelating agent, lower alcohol and nonionic surfactant are those specifically mentioned hereinabove.

For use as a hair setting agent, such as mousse, the hair treatment composition of the present invention is formulated as follows: 0.1 to 10% by weight of a cationic surfactant comprising said quaternary ammonium salt (A) or the mixture of said salt (A) and the tertiary amine salt (B), 0.5 to 20% by weight of the macromolecular compound, 0.5 to 10% by weight of the oil, 0 to 5% by weight of the humectant, 0 to 5% by weight of the chelating agent, 0.5 to 30% by weight of the lower alcohol, 0 to 5% by weight of the nonionic surfactant, 0 to 5% by weight of an additive selected from the group consisting of perfumes, colorants, preservatives and ultraviolet absorbers, and 15 to 98.4% by weight of water.

In addition, such an anionic surfactant, amphoteric surfactant and/or cationic surfactant as specifically mentioned above may be used additionally within limits within which the effects of the present invention will not be sacrificed. For use as a hair setting agent, the composition contains 0.1 to 10% by weight of total cationic surfactants based on the composition.

The hair treatment composition of the present invention generally has a pH of 3 to 9. If the pH is below 3 or above 9, the counter ion may undergo exchange, which may lead to increased irritation to skin, or worsened posttreatment feel of hair (worsened smooth flow and moist feel of hair), or failure of the quaternary ammonium salt of the present invention to show its performance characteristics to a satisfactory extent.

The following examples illustrate the present invention in further detail. They are, however, by no means limitative of the scope of the present invention.

PRODUCTION EXAMPLE 1

An agitating type autoclave was charged with 99 g of dimethyl carbonate, 353 g of behenyldimethylamine and 170 g of methanol, and the reaction was allowed to proceed at a reaction temperature of 110 to 130° C. for 12 hours with stirring. Then, 147 g of glutamic acid was charged and the salt exchange reaction was effected while allowing decarboxylation to proceed at a reaction temperature of 60 to 80° C. Thereafter, 1,542 g of water was added and the methanol and unreacted dimethyl carbonate were removed in a nitrogen atmosphere at a temperature of 60 to 90° C. and a degree of pressure reduction of 100 mmHg. Adjustment of the pH to 5 with citric acid gave the glutamic acid salt of the compound (a1) specified in Table 1 under (5).

PRODUCTION EXAMPLE 2

An agitating type autoclave was charged with 353 g of behenyldimethylamine and 1,211 g of water, and 53 g of methyl chloride was blown into the resulting mixture with stirring over 3 hours while the reaction temperature was maintained at 80 to 90° C., followed by 3 hours of maturation. The unreacted methyl chloride was then distilled off, and 169 g of sodium glutamate and 331 g of water were added, and salt exchange was effected at a treatment temperature of 80 to 90° C. in a nitrogen atmosphere. Adjustment of the pH to 5 with citric acid gave the glutamic acid salt of the compound (a1) specified in Table 1 under (5).

PRODUCTION EXAMPLE 3

An agitating type autoclave was charged with 99 g of dimethyl carbonate, 353 g of behenyldimethylamine and 170 g of methanol, and the reaction was allowed to proceed with stirring at a reaction temperature of 110 to 130° C. for 12 hours. Then, 133 g of aspartic acid was added, and salt exchange was effected while allowing the decarboxylation reaction to proceed at a reaction temperature of 60 to 80° C. Thereafter, 1,542 g of water was added, and the methanol and unreacted dimethyl carbonate were removed in a nitrogen atmosphere at a temperature of 60 to 90° C. and a pressure reduction degree of 100 mmHg. The subsequent adjustment of the pH to 5 with citric acid gave the aspartic acid salt of the compound (a1) specified in Table 1 under (5).

PRODUCTION EXAMPLE 4

An agitating type autoclave was charged with 99 g of dimethyl carbonate, 300 g of behenyldimethylamine, 45 g of stearyldimethylamine and 170 g of methanol, and the reaction was allowed to proceed with stirring at a reaction temperature of 110 to 130° C. for 12 hours. Then, 147 g of glutamic acid was added, and the salt exchange reaction was effected while allowing the decarboxylation reaction to proceed at a temperature of 60 to 80° C. Thereafter, 1,542 g of water was added and the methanol and unreacted dimethyl carbonate were removed in a nitrogen atmosphere at a temperature of 60 to 90° C. and a pressure reduction degree of 100 mmHg. The subsequent adjustment of the pH to 5 with citric acid gave the glutamic acid salt of the compound (a1) specified in Table 1 under (11).

PRODUCTION EXAMPLE 5

An agitating type reactor equipped with a thermometer was charged with 340 g of behenic acid, 134 g of dimethylaminoethanol and an adequate amount of p-toluenesulfonic acid as catalyst, and the dehydration condensation reaction was effected at a reaction temperature of 140 to 150° C., and the unreacted dimethylaminoethanol was distilled off. Then, an agitating type autoclave was charged with 411 g of the dehydration condensate obtained, 99 g of dimethyl carbonate and 170 g of isopropyl alcohol, and the reaction was allowed to proceed with stirring at a reaction temperature of 110 to 130° C. for 12 hours. Then, 147 g of glutamic acid was added, and salt exchange was effected while allowing the decarboxylation reaction to proceed at a reaction temperature of 60 to 80° C. Thereafter, 1,716 g of water was added, and the isopropyl alcohol and unreacted dimethyl carbonate were removed in a nitrogen atmosphere at a temperature of 60 to 90° C. and a pressure reduction degree of 100 mmHg. Adjustment of the pH to 5 with citric acid gave the glutamic acid salt of the compound (2a) specified in Table 2 under (20).

PRODUCTION EXAMPLE 6

An agitating type reactor equipped with a thermometer was charged with 340 g of behenic acid, 134 g of dimethylaminoethanol and an appropriate amount of p-toluenesulfonic acid as catalyst, and the dehydration condensation reaction was allowed to proceed at a reaction temperature of 140 to 150° C. The unreacted dimethylaminoethanol was distilled off. Thereafter, an agitating type autoclave was charged with 411 g of the dehydration condensate obtained and 308 g of isopropyl alcohol, and 53 g of methyl chloride was blown into the mixture with stirring over 3 hours while maintaining the reaction temperature at 80 to 90° C., followed by 3 hours of maturation. After removal of the unreacted methyl chloride by distillation, 169 g of sodium glutamate and 1,716 g of water were added, and the isopropyl alcohol was removed while effecting salt exchange in a nitrogen atmosphere at a treatment temperature of 80 to 90° C. and a pressure reduction degree of 100 mmHg. Adjustment of the pH to 5 with citric acid gave the glutamic acid salt of the compound (a2) specified in Table 2 under (20).

PRODUCTION EXAMPLE 7

An agitating type reactor equipped with a thermometer was charged with 340 g of behenic acid, 134 g of dimethylaminoethanol and a catalytic amount of p-toluenesulfonic acid, and the dehydration condensation reaction was allowed to proceed at a reaction temperature of 140 to 150° C. The unreacted dimethylaminoethanol was distilled off. Thereafter, an agitating type autoclave was charged with 411 g of the dehydration condensate obtained, 99 g of dimethyl carbonate and 170 g of isopropyl alcohol, and the reaction was allowed to proceed with stirring at a reaction temperature of 110 to 130° C. for 12 hours. Then, 133 g of aspartic acid was added, and salt exchange was effected while allowing the decarboxylation reaction to proceed at a reaction temperature of 60 to 80° C. Thereafter, 1,716 g of water was added, and the isopropyl alcohol and unreacted dimethyl carbonate were removed in a nitrogen atmosphere at a temperature of 60 to 90° C. and a pressure reduction degree of 100 mmHg. Adjustment of the pH to 5 with citric acid gave the aspartic acid salt of the compound (a2) specified in Table 2 under (20).

PRODUCTION EXAMPLE 8

An agitating type reactor equipped with a thermometer was charged with 289 g of behenic acid, 43 g of stearic acid, 134 g of dimethylaminoethanol and a catalytic amount of p-toluenesulfonic acid, and the dehydration condensation reaction was allowed to proceed at a reaction temperature of 140 to 150° C. The unreacted dimethylaminoethanol was distilled off. Thereafter, an agitating type autoclave was charged with 411 g of the dehydration condensate obtained, 99 g of dimethyl carbonate and 170 g of isopropyl alcohol, and the reaction was allowed to proceed at a reaction temperature of 110 to 130° C. for 12 hours. Then, 147 g of glutamic acid was added, and salt exchange was effected while allowing the decarboxylation reaction to proceed at a reaction temperature of 60 to 80° C. Thereafter, 1,716 g of water was added, and the isopropyl alcohol and unreacted dimethyl carbonate were removed in a nitrogen atmosphere at a temperature of 60 to 90° C. and a pressure reduction degree of 100 mmHg. Adjustment of the pH to 5 with citric acid gave the glutamic acid salt of the compound (a2) specified in Table 3 under (26).

PRODUCTION EXAMPLE 9

An agitating type autoclave was charged with 99 g of dimethyl carbonate, 297 g of stearyldimethylamine and 170 g of methanol, and the reaction was allowed to proceed with stirring at a reaction temperature of 110 to 130° C. for 12 hours. Then, 147 g of glutamic acid was added, and salt exchange was effected while allowing the decarboxylation reaction to proceed at a reaction temperature of 60 to 80° C. Thereafter, 1,374 g of water was added, and the methanol and unreacted dimethyl carbonate were removed in a nitrogen atmosphere at a temperature of 60 to 90° C. and a pressure reduction degree of 100 mmHg. Adjustment of the pH to 5 with citric acid gave the glutamic acid salt of the compound (a1) specified in Table 1 under (4).

PRODUCTION EXAMPLE 10

An agitating type autoclave was charged with 99 g of dimethyl carbonate, 292 g of hardened beef tallow alkyldimethylamine and 170 g of methanol, and the reaction was allowed to proceed with stirring at a reaction temperature of 110 to 130° C. for 12 hours. Then, 147 g of glutamic acid was added, and salt exchange was effected while allowing the decarboxylation reaction to proceed at a reaction temperature of 60 to 80° C. Thereafter, 1,374 g of water was added, and the methanol and unreacted dimethyl carbonate were removed in a nitrogen atmosphere at a temperature of 60 to 90° C. and a pressure reduction degree of 100 mmHg. Adjustment of the pH to 5 with citric acid gave the glutamic acid salt of the compound (a1) specified in Table 1 under (14).

PRODUCTION EXAMPLE 11

An agitating type reactor equipped with a thermometer was charged with 284 g of stearic acid, 134 g of dimethylaminoethanol and a catalytic amount of p-toluenesulfonic acid, and the dehydration condensation reaction was allowed to proceed at a reaction temperature of 140 to 150° C. The unreacted dimethylaminoethanol was distilled off. Then, an agitating type autoclave was charged with 355 g of dehydration condensate obtained, 99 g of dimethyl carbonate and 170 g of isopropyl alcohol, and the reaction was allowed to proceed with stirring at a reaction temperature of 110 to 130° C. for 12 hours. Then, 147 g of glutamic acid was added, and salt exchange was effected while allowing the decarboxylation reaction to proceed at a reaction temperature of 60 to 80° C. Thereafter, 1,548 g of water was added, and the isopropyl alcohol and unreacted dimethyl carbonate were removed in a nitrogen atmosphere at a temperature of 60 to 90° C. and a pressure reduction degree of 100 mmHg. Adjustment of the pH to 5 with citric acid gave the glutamic acid salt of the compound (a2) specified in Table 2 under (19).

PRODUCTION EXAMPLE 12

An agitating type reactor equipped with a thermometer was charged with 279 g of hardened beef tallow fatty acid, 134 g of dimethylaminoethanol and a catalytic amount of p-toluenesulfonic acid, and the dehydration condensation reaction was allowed to proceed at a reaction temperature of 140 to 150° C. The unreacted dimethylaminoethanol was distilled off. Then, an agitating type autoclave was charged with 355 g of the dehydration condensate obtained, 99 g of dimethyl carbonate and 170 g of isopropyl alcohol, and the reaction was allowed to proceed with stirring at a temperature of 110 to 130° C. for 12 hours. Thereafter, 147 g of glutamic acid was added, and salt exchange was effected under decarboxylation at a reaction temperature of 60 to 80° C. Then, 1,548 g of water was added, and the isopropyl alcohol and unreacted dimethyl carbonate were removed in a nitrogen atmosphere at a temperature of 60 to 90° C. and a pressure reduction degree of 100 mmHg. Adjustment of the pH to 5 with citric acid gave the glutamic acid salt of the compound (a2) specified in Table 3 under (30).

PRODUCTION EXAMPLE 13

An agitating type autoclave was charged with 99 g of dimethyl carbonate, 269 g of cetyldimethylamine and 170 g of methanol, and the reaction was allowed to proceed with stirring at a reaction temperature of 110 to 115° C. for 12 hours. Then, 147 g of glutamic acid was added, and salt exchange was effected under decarboxylation at a reaction temperature of 60 to 80° C. Thereafter, 1,290 g of water was added, and the methanol and unreacted dimethyl carbonate were removed in a nitrogen atmosphere at a temperature of 60 to 90° C. and a pressure reduction degree of 100 mmHg. Adjustment of the pH to 5 with citric acid gave the glutamic acid salt of the compound (a1) specified in Table 1 under (3).

PRODUCTION EXAMPLE 14

An agitating type reactor equipped with a thermometer was charged with 340 g of behenic acid, 134 g of dimethylaminoethanol and a catalytic amount of p-toluenesulfonic acid, and the dehydration condensation reaction was allowed to proceed at a reaction temperature of 140 to 150° C. The unreacted dimethylaminoethanol was distilled off. Then, 147 g of glutamic acid and 1,674 g of water were added, and neutralization was effected in a nitrogen atmosphere at a treatment temperature of 80 to 90° C., followed by pH adjustment to 5 with citric acid, to give the compound (b) specified in Table 6 under (120) as neutralized with glutamic acid.

PRODUCTION EXAMPLE 15

An agitating type reactor equipped with a thermometer was charged with 340 g of behenic acid, 134 g of dimethylaminoethanol and a catalytic amount of p-toluenesulfonic acid, and the dehydration condensation reaction was allowed to proceed at a reaction temperature of 140 to 150° C. The unreacted dimethylaminoethanol was distilled off. Then, 133 g of aspartic acid and 1,674 g of water were added, and neutralization was effected in a nitrogen atmosphere at a treatment temperature of 80 to 90° C., followed by pH adjustment to 5 with citric acid, to give the compound (b) specified in Table 7 under (120) as neutralized with aspartic acid.

PRODUCTION EXAMPLE 16

An agitating type reactor equipped with a thermometer was charged with 289 g of behenic acid, 43 g of stearic acid, 134 g of dimethylaminoethanol and a catalytic amount of p-toluenesulfonic acid, and the dehydration condensation reaction was allowed to proceed at a reaction temperature of 140 to 150° C. The unreacted dimethylaminoethanol was distilled off. Then, 147 g of glutamic acid and 1,674 g of water were added, and neutralization was effected in a nitrogen atmosphere at a treatment temperature of 80 to 90° C., followed by pH adjustment to 5 with citric acid, to give the compound (b) specified in Table 7 under (136) as neutralized with glutamic acid.

PRODUCTION EXAMPLE 17

An agitating type reactor equipped with a thermometer was charged with 340 g of behenic acid and 153 g of dimethylaminopropylamine, and the dehydration condensation reaction was allowed to proceed at a reaction temperature of 140 to 150° C. The unreacted dimethylaminopropylamine was distilled off. Then, 147 g of glutamic acid and 1,713 g of water were added, and neutralization was effected in a nitrogen atmosphere at a treatment temperature of 80 to 90° C., followed by pH adjustment to 5 with citric acid, to give the compound (b) specified. in Table 7 under (126) as neutralized with glutamic acid.

PRODUCTION EXAMPLE 18

An agitating type reactor equipped with a thermometer was charged with 340 g of behenic acid and 153 g of dimethylaminopropylamine, and the dehydration condensation reaction was allowed to proceed at a reaction temperature of 140 to 150° C. The unreacted dimethylaminopropylamine was distilled off. Then, 147 g of aspartic acid and 1,713 g of water were added, and neutralization was effected in a nitrogen atmosphere at a treatment temperature of 80 to 90° C., followed by pH adjustment to 5 with citric acid, to give the compound (b) specified in Table 7 under (126) as neutralized with aspartic acid.

PRODUCTION EXAMPLE 19

An agitating type reactor equipped with a thermometer was charged with 289 g of behenic acid, 43 g of stearic acid and 153 g of dimethylaminopropylamine, and the dehydration condensation reaction was allowed to proceed at a reaction temperature of 140 to 150° C. The unreacted dimethylaminopropylamine was distilled off. Then, 147 g of glutamic acid and 1,713 g of water were added, and neutralization was effected in a nitrogen atmosphere at a treatment temperature of 80 to 90° C., followed by pH adjustment to 5 with citric acid, to give the compound (b) specified in Table 8 under (137) as neutralized with glutamic acid.

PRODUCTION EXAMPLE 20

An agitating type reactor equipped with a thermometer was charged with 284 g of stearic acid, 134 g of dimethylaminoethanol and a catalytic amount of p-toluenesulfonic acid, and the dehydration condensation reaction was allowed to proceed at a reaction temperature of 140 to 150° C. The unreacted dimethylaminoethanol was distilled off. Then, 147 g of glutamic acid and 1,506 g of water were added, and neutralization was effected in a nitrogen atmosphere at a treatment temperature of 80 to 90° C., followed by pH adjustment to 5 with citric acid, to give the compound (b) specified in Table 7 under (119) as neutralized with glutamic acid.

PRODUCTION EXAMPLE 21

An agitating type reactor equipped with a thermometer was charged with 279 g of hardened beef tallow fatty acid, 134 g of dimethylaminoethanol and a catalytic amount of p-toluenesulfonic acid, and the dehydration condensation reaction was allowed to proceed at a reaction temperature of 140 to 150° C. The unreacted dimethylaminoethanol was distilled off. Then, 147 g of glutamic acid and 1,674 g of water were added, and neutralization was effected in a nitrogen atmosphere at a treatment temperature of 80 to 90° C., followed by pH adjustment to 5 with citric acid, to give the compound (b) specified in Table 8 under (138) as neutralized with glutamic acid.

PRODUCTION EXAMPLE 22

An agitating type reactor equipped with a thermometer was charged with 284 g of stearic acid and 153 g of dimethylaminopropylamine, and the dehydration condensation reaction was allowed to proceed at a reaction temperature of 140 to 150° C. The unreacted dimethylaminopropylamine was distilled off. Then, 147 g of glutamic acid and 1,545 g of water were added, and neutralization was effected in a nitrogen atmosphere at a treatment temperature of 80 to 90° C., followed by pH adjustment to 5 with citric acid, to give the compound (b) specified in Table 7 under (125) as neutralized with glutamic acid.

PRODUCTION EXAMPLE 23

An agitating type reactor equipped with a thermometer was charged with 279 g of hardened beef tallow fatty acid and 153 g of dimethylaminopropylamine, and the dehydration condensation reaction was allowed to proceed at a reaction temperature of 140 to 150° C. The unreacted dimethylaminopropylamine was distilled off. Then, 147 g of glutamic acid and 1,545 g of water were added, and neutralization was effected in a nitrogen atmosphere at a treatment temperature of 80 to 90° C., followed by pH adjustment to 5 with citric acid, to give the compound (b) specified in Table 8 under (139) as neutralized with glutamic acid.

PRODUCTION EXAMPLE 24

An agitating type reactor equipped with a thermometer was charged with 340 g of behenic acid, 134 g of dimethylaminoethanol and a catalytic amount of p-toluenesulfonic acid, and the dehydration condensation reaction was allowed to proceed at a reaction temperature of 140 to 150° C. The unreacted dimethylaminoethanol was distilled off. Then, an agitating type autoclave was charged with 411 g of the dehydration condensate obtained, 72 g of dimethyl carbonate and 170 g of isopropyl alcohol, and the reaction was allowed to proceed with stirring at a reaction temperature of 110 to 130° C. for 12 hours. Then, 147 of glutamic acid was added, and salt exchange was effected under decarboxylation at a reaction temperature of 60 to 80° C. Thereafter, 1,708 g of water was added, and the isopropyl alcohol and unreacted dimethyl carbonate were removed in a nitrogen atmosphere at a temperature of 60 to 90° C. and a pressure reduction degree of 100 mmHg, followed by pH adjustment to 5 with citric acid, to give the glutamic acid salt of the compound (2a) specified in Table under (20) and the compound (b) specified in Table 7 under (120) as neutralized with glutamic acid.

PRODUCTION EXAMPLE 25

An agitating type reactor equipped with a thermometer was charged with 326 g of behenyl alcohol and 94.5 g of monochloroacetic acid, and the dehydration condensation reaction was allowed to proceed at a reaction temperature of 90 to 100° C. Thereafter, an agitating type autoclave was charged with 402.5 of the dehydration condensate obtained and 308 g of isopropyl alcohol, and 70 g of trimethylamine was added to the mixture over 3 hours with stirring while maintaining the reaction temperature at 80 to 90° C., followed by further 3 hours of maturation. After removal of the unreacted trimethylamine by distillation, 169 g of sodium glutamate and 1,755 g of water were added, and the isopropyl alcohol was removed under salt exchange in a nitrogen atmosphere at a treatment temperature of 80 to 90° C. and a pressure reduction degree of 100 mmHg. Adjustment of the pH to 5 with citric acid gave the glutamic acid salt of the compound (a2) specified in Table 2 under (25).

PRODUCTION EXAMPLE 26

An agitating type reactor equipped with a thermometer was charged with 340 g of behenic acid and 153 g of dimethylaminopropylamine, and the dehydration condensation reaction was allowed to proceed at a reaction temperature of 140 to 150° C. The unreacted dimethylaminopropylamine was distilled off. Thereafter, an agitating type autoclave was charged with 424 g of the dehydration condensate obtained, 99 g of dimethyl carbonate and 170 g of isopropyl alcohol, and the reaction was allowed to proceed with stirring at a reaction temperature of 110 to 130° C. for 12 hours. Then, 147 g of glutamic acid was added, and salt exchange was effected under decarboxylation at a reaction temperature of 60 to 80° C. Thereafter, 1,755 g of water was added, and the isopropyl alcohol and unreacted dimethyl carbonate were removed in a nitrogen atmosphere at a temperature of 60 to 90° C. and a pressure reduction degree of 100 mmHg, followed by pH adjustment to 5 with citric acid, to give the glutamic acid salt of the compound (a3) specified in Table 4 under (34).

PRODUCTION EXAMPLE 27

An agitating type reactor equipped with a thermometer was charged with 340 g of behenic acid and 153 g of dimethylaminopropylamine, and the dehydration condensation reaction was allowed to proceed at a reaction temperature of 140 to 150° C. The unreacted dimethylaminopropylamine was distilled off. Thereafter, an agitating type autoclave was charged with 424 g of the dehydration condensate obtained and 308 g of isopropyl alcohol, and 53 g of methyl chloride was blown into the mixture over 3 hours with stirring while maintaining the reaction temperature at 80 to 90° C., followed by further 3 hours of maturation. After removal of the unreacted methyl chloride by distillation, 169 g of sodium glutamate and 1,755 g of water were added, and the isopropyl alcohol was removed under salt exchange in a nitrogen atmosphere at a treatment temperature of 80 to 90° C. and a pressure reduction degree of 100 mmHg, followed by pH adjustment to 5 with citric acid, to give the glutamic acid salt of the compound (a3) specified in Table 4 under (34).

PRODUCTION EXAMPLE 28

An agitating type reactor equipped with a thermometer was charged with 340 g of behenic acid and 153 g of dimethylaminopropylamine, and the dehydration condensation reaction was allowed to proceed at a reaction temperature of 140 to 150° C. The unreacted dimethylaminopropylamine was distilled off. Thereafter, an agitating type autoclave was charged with 424 g of the dehydration condensate obtained, 99 g of dimethyl carbonate and 170 g of isopropyl alcohol, and the reaction was allowed to proceed with stirring at a reaction temperature of 110 to 130° C. for 12 hours. Then, 133 g of aspartic acid was added, and salt exchange was effected under decarboxylation at a reaction temperature of 60 to 80° C. Thereafter, 1,755 g of water was added, and the isopropyl alcohol and unreacted dimethyl carbonate were removed in a nitrogen atmosphere at a temperature of 60 to 90° C. and a pressure reduction degree of 100 mmHg, followed by pH adjustment to 5 with citric acid, to give the aspartic acid salt of the compound (a3) specified in Table 4 under (34).

PRODUCTION EXAMPLE 29

An agitating type reactor equipped with a thermometer was charged with 289 g of behenic acid, 43 g of stearic acid and 153 g of dimethylaminopropylamine, and the dehydration condensation reaction was allowed to proceed at a reaction temperature of 140 to 150° C. The unreacted dimethylaminopropylamine was distilled off. Thereafter, an agitating type autoclave was charged with 424 g of the dehydration condensate obtained, 99 g of dimethyl carbonate and 170 g of isopropyl alcohol, and the reaction was allowed to proceed with stirring at a reaction temperature of 110 to 130° C. for 12 hours. Then, 147 of glutamic acid was added, and salt exchange was effected under decarboxylation at a reaction temperature of 60 to 80° C. Thereafter, 1,755 g of water was added, and the isopropyl alcohol and unreacted dimethyl carbonate were removed in a nitrogen atmosphere at a temperature of 60 to 90° C. and a pressure reduction degree of 100 mmHg, followed by pH adjustment to 5 with citric acid, to give the glutamic acid salt of the compound (a3) specified in Table 5 under (42).

PRODUCTION EXAMPLE 30

An agitating type reactor equipped with a thermometer was charged with 284 g of stearic acid and 153 g of dimethylaminopropylamine, and the dehydration condensation reaction was allowed to proceed at a reaction temperature of 140 to 150° C. The unreacted dimethylaminopropylamine was distilled off. Thereafter, an agitating type autoclave was charged with 368 g of the dehydration condensate obtained, 99 g of dimethyl carbonate and 170 g of isopropyl alcohol, and the reaction was allowed to proceed with stirring at a reaction temperature of 110 to 130° C. for 12 hours. Then, 147 g of glutamic acid was added, and salt exchange was effected while allowing the decarboxylation reaction to proceed at a reaction temperature of 60 to 80° C. Thereafter, 1,587 g of water was added, and the isopropyl alcohol and unreacted dimethyl carbonate were removed in a nitrogen atmosphere at a temperature of 60 to 90° C. and a pressure reduction degree of 100 mmHg, followed by pH adjustment to 5 with citric acid, to give the glutamic acid salt of the compound (a3) specified in Table 4 under (33).

PRODUCTION EXAMPLE 31

An agitating type reactor equipped with a thermometer was charged with 279 g of hardened beef tallow fatty acid and 153 g of dimethylaminopropylamine, and the dehydration condensation reaction was allowed to proceed at a reaction temperature of 140 to 150° C. The unreacted dimethylaminopropylamine was distilled off. Thereafter, an agitating type autoclave was charged with 368 g of the dehydration condensate obtained, 99 g of dimethyl carbonate and 170 g of isopropyl alcohol, and the reaction was allowed to proceed with stirring at a reaction temperature of 110 to 130° C. for 12 hours. Then, 147 g of glutamic acid was added, and salt exchange was effected under decarboxylation at a reaction temperature of 60 to 80° C. Then, 1,587 g of water was added, and the isopropyl alcohol and unreacted dimethyl carbonate were removed in a nitrogen atmosphere at a temperature of 60 to 90° C. and a pressure reduction degree of 100 mmHg, followed by pH adjustment to 5 with citric acid, to give the glutamic acid salt of the compound (a3) specified in Table 4 under (33).

PRODUCTION EXAMPLE 32

An agitating type reactor equipped with a thermometer was charged with 340 g of behenic acid and 153 g of dimethylaminopropylamine, and the dehydration condensation reaction was allowed to proceed at a reaction temperature of 140 to 150° C. The unreacted dimethylaminopropylamine was distilled off. Thereafter, an agitating type autoclave was charged with 424 g of the dehydration condensate obtained, 72 g of dimethyl carbonate and 170 g of isopropyl alcohol, and the reaction was allowed to proceed with stirring while maintaining the reaction temperature at 110 to 115° C. for 12 hours. Then, 147 g of glutamic acid was added, and salt exchange was effected under decarboxylation at a reaction temperature of 60 to 80° C. Then, 1,741 g of water was added, and the isopropyl alcohol and unreacted dimethyl carbonate were removed in a nitrogen atmosphere at a temperature of 60 to 90° C. and a pressure reduction degree of 100 mmHg, followed by pH adjustment to 5 with citric acid, to give the glutamic acid salt of the compound (a3) specified in Table 4 under (34) and the compound (b) specified in Table 6 under (126) as neutralized with glutamic acid.

PRODUCTION EXAMPLE 33

An agitating type reactor equipped with a thermometer was charged with 325 g of behenylamine and 94.5 g of monochloroacetic acid, and the dehydration condensation reaction was allowed to proceed at a reaction temperature of 90 to 100° C. Thereafter, an agitating type autoclave was charged with 401.5 g of the dehydration condensate obtained and 308 g of isopropyl alcohol, and 70 g of trimethylamine was added over 3 hours with stirring while maintaining the reaction temperature at 80 to 90° C., followed by further 3 hours of maturation. After removal of the unreacted trimethylamine by distillation, 169 g of sodium glutamate and 1,755 g of water were added, and the isopropyl alcohol was removed while effecting salt exchange in a nitrogen atmosphere at a treatment temperature of 80 to 90° C. and a pressure reduction degree of 100 mmHg. Adjustment of the pH to 5 with citric acid gave the glutamic acid salt of the compound (a3) specified in Table 4 under (39).

EXAMPLES 1 TO 28 AND COMPARATIVE EXAMPLES 1 TO 4

Hair treatment compositions according to the present invention and hair treatment compositions for comparison were prepared by using the compounds described in Tables 1 to 8 as produced by the procedures shown in Production Examples 1 to 33 and adding a perfume and a colorant, each in an appropriate amount, to the formulations given in Tables 9 to 14 (in terms of parts by weight), adjusting the pH to 5 with citric acid and adding water (remainder portion) to make the whole amount 100 parts, and tested for skin irritation, feel, biodegradability, thickening effect and emulsion stability. The results thus obtained are shown in Tables 9 to 14.

TABLE 9

| Component | EXAMPLE 1 | 2 | 3 | 4 | 5 | 6 |
|---|---|---|---|---|---|---|
| | Formulation (part by weight) | | | | | |
| (A1) or (A2) | (5) + Gl 0.99 | (5) + AS 0.99 | (4) + Gl 0.99 | (3) + Gl 0.99 | (20) + Gl 0.99 | (20) + As 0.99 |
| (B) | 105 + Gl 0.01 | 105 + As 0.01 | 104 + Gl 0.0 | 103 + Gl 0.0 | 120 + Gl 0.01 | 120 + As 0.01 |
| E1 | — | — | — | 1.00 | — | — |
| E2 | 3.00 | 3.00 | 3.00 | 2.00 | 3.00 | 2.00 |
| E3 | — | — | — | — | — | 1.00 |
| F1 | 2.00 | — | 2.00 | 2.00 | — | 2.00 |
| F2 | — | 2.00 | — | — | 2.00 | — |
| Emulsifier | 1.00 | 1.00 | 1.00 | 1.00 | 1.00 | 1.00 |
| Humectant | 3.00 | 3.00 | 3.00 | 3.00 | 3.00 | 3.00 |
| Low silicone | 2.00 | — | 2.00 | 2.00 | 2.00 | — |
| High silicone | — | 1.00 | — | — | — | 1.00 |
| G1 | — | 0.50 | — | — | 0.50 | 0.50 |
| G2 | 0.50 | — | 0.50 | 0.50 | — | — |
| H1 | 0.50 | — | 0.50 | 0.50 | — | 0.50 |
| H2 | — | 0.50 | — | — | 0.50 | — |
| Chelating agent | 0.10 | 0.10 | 0.10 | 0.10 | 0.10 | 0.10 |
| J1 | — | 1.00 | — | — | 1.00 | — |
| J2 | 1.00 | — | 1.00 | 1.00 | — | 1.00 |
| water | Added to make the whole amount 100 parts | | | | | |
| Results of performance evaluation | | | | | | |
| Skin irritation | 1 | 1 | 2 | 4 | 1 | 1 |
| Feel | 49 | 39 | 38 | 36 | 40 | 39 |
| Biodegradability | ○ | ○ | ○ | ○ | ⊙ | ⊙ |
| Thickening effect | ○ | ○ | ○ | ○ | ○ | ○ |
| Emulsion stability | ○ | ○ | ○ | ○ | ○ | ○ |

TABLE 10

| Component | EXAMPLE 7 | 8 | 9 | 10 | 11 | 12 |
|---|---|---|---|---|---|---|
| | Formulation (part by weight) | | | | | |
| (A1) or (A2) | (19) + 0.99 | (20) + Gl 0.80 | (20) + Gl 0.80 | (20) + As 0.80 | (7) + Gl 0.99 | (22) + Gl 0.99 |
| (B) | 119 + Gl 0.01 | 120 + Gl 0.20 | 125 + Gl 0.20 | 120 + As 0.20 | 107 + Gl 0.01 | 122 + Gl 0.01 |
| E1 | — | — | — | — | — | — |
| E2 | 2.00 | 3.00 | 1.00 | 3.00 | 3.00 | — |
| E3 | 1.00 | — | 2.00 | — | — | 3.00 |
| F1 | 2.00 | 2.00 | — | 2.00 | 2.00 | — |
| F2 | — | — | 2.00 | — | — | 1.00 |
| Emulsifier | 1.00 | 1.00 | 1.00 | 1.00 | — | 0.50 |
| Humectant | 3.00 | 3.00 | 3.00 | 3.00 | 3.00 | 3.00 |
| Low silicone | 2.00 | 2.00 | — | 1.00 | 2.00 | — |
| High silicone | — | — | 2.00 | — | — | 1.00 |
| G1 | — | 0.50 | — | — | 0.50 | — |
| G2 | 0.50 | — | 0.50 | 0.50 | — | 0.50 |
| H1 | 0.50 | — | 0.50 | 0.50 | — | 1.00 |
| H2 | — | 0.50 | — | — | 1.00 | — |
| Chelating agent | 0.10 | 0.10 | 0.10 | 0.10 | 0.10 | 0.10 |
| J1 | 1.00 | 1.00 | 0.50 | 1.00 | 2.00 | — |
| J2 | — | — | — | — | — | 2.00 |
| water | Added to make the whole amount 100 parts | | | | | |
| Results of performance evaluation | | | | | | |
| Skin irritation | 2 | 1 | 1 | 1 | 2 | 2 |
| Feel | 38 | 40 | 39 | 39 | 37 | 35 |
| Biodegradability | ⊙ | ⊙ | ⊙ | ⊙ | ○ | ○ |
| Thickening effect | ○ | ○ | ○ | ○ | ○ | ○ |
| Emulsion stability | ○ | ○ | ○ | ○ | ○ | ○ |

TABLE 11

| Component | EXAMPLE 13 | 14 | 15 | 16 | 17 | 18 |
|---|---|---|---|---|---|---|
| | Formulation (part by weight) | | | | | |
| (A1) or (A2) | (25) + Gl 0.99 | (11) + Gl 0.99 | (26) + Gl 0.99 | (30) + Gl 0.99 | (5) + Gl 1.00 | (20) + Gl 1.00 |
| (B) | 131 + Gl 0.01 | 111 + Gl 0.01 | 136 + Gl 0.01 | 138 + Gl 0.01 | — | — |
| E1 | — | — | — | — | — | — |
| E2 | — | 3.00 | 2.00 | 3.00 | 3.00 | 3.00 |
| E3 | 3.00 | — | 1.00 | — | — | — |
| F1 | 1.00 | 2.00 | — | 2.00 | 2.00 | 2.00 |
| F2 | — | — | 1.00 | — | — | — |
| Emulsifier | 0.50 | — | 0.50 | 0.50 | 0.50 | 0.50 |
| Humectant | 3.00 | 3.00 | 3.00 | 3.00 | 3.00 | 3.00 |
| Low silicone | — | 2.00 | — | 2.00 | 2.00 | 2.00 |
| High silicone | 1.00 | — | 2.00 | — | — | — |
| G1 | 0.50 | 0.50 | — | — | 0.50 | 0.50 |
| G2 | — | — | 0.50 | 0.50 | — | — |
| H1 | — | — | 1.00 | 1.00 | — | — |
| H2 | 1.00 | 1.00 | — | — | 1.00 | 1.00 |
| Chelating agent | 0.10 | 0.10 | 0.10 | 0.10 | 0.10 | 0.10 |
| J1 | 2.00 | 2.00 | — | 1.50 | 2.00 | 2.00 |
| J2 | — | — | 2.00 | — | — | — |
| water | Added to make the whole amount 100 parts | | | | | |
| Results of performance evaluation | | | | | | |
| Skin irritation | 2 | 2 | 2 | 2 | 2 | 2 |
| Feel | 39 | 39 | 38 | 37 | 40 | 40 |
| Biodegradability | ⊙ | ○ | ⊙ | ⊙ | ○ | ⊙ |
| Thickening effect | ○ | ○ | ○ | ○ | ○~Δ | ○~Δ |
| Emulsion stability | ○ | ○ | ○ | ○ | ○~Δ | ○~Δ |

TABLE 12

| Component | EXAMPLE 19 | 20 | 21 | 22 | 23 |
|---|---|---|---|---|---|
| | Formulation (part by weight) | | | | |
| (A3) | (34) + Gl 0.99 | (34) + As 0.99 | (33) + Gl 0.99 | (34) + Gl 0.80 | (34) + Gl 0.80 |
| (B) | 126 + Gl 0.01 | 126 + As 0.01 | 125 + Gl 0.01 | 126 + Gl 0.20 | 119 + Gl 0.20 |
| E1 | — | 1.00 | 3.00 | — | 1.00 |
| E2 | 3.00 | 2.00 | — | — | 2.00 |
| E3 | — | — | — | 3.00 | — |
| F1 | — | — | 2.00 | 2.00 | 2.00 |
| F2 | 2.00 | 2.00 | — | — | — |
| Emulsifier | 1.00 | 1.00 | 1.00 | 1.00 | 1.00 |
| Humectant | 3.00 | 3.00 | 3.00 | 3.00 | 3.00 |
| Low silicone | — | — | — | — | 2.00 |
| High silicone | 1.00 | 1.00 | 1.00 | 1.00 | — |
| G1 | — | 0.50 | — | 0.50 | — |
| G2 | 0.50 | — | 0.50 | — | 0.50 |
| H1 | — | 0.50 | 0.50 | — | — |
| H2 | 0.50 | — | — | 0.50 | 0.50 |
| Chelating agent | 0.10 | 0.10 | 0.10 | 0.10 | 0.10 |
| J1 | — | 1.00 | 1.00 | — | 1.00 |
| J2 | 1.00 | — | — | 1.00 | — |
| water | Added to make the whole 100 parts | | | | |
| Results of performance evaluation | | | | | |
| Skin irritation | 1 | 1 | 2 | 1 | 1 |
| Feel | 40 | 39 | 38 | 40 | 39 |
| Biodegradability | ⊙ | ⊙ | ⊙ | ⊙ | ⊙ |

TABLE 12-continued

| | EXAMPLE | | | | |
|---|---|---|---|---|---|
| | 19 | 20 | 21 | 22 | 23 |
| Component | Formulation (part by weight) | | | | |
| Thickening effect | ○ | ○ | ○ | ○ | ○ |
| Emulsion stability | ○ | ○ | ○ | ○ | ○ |

TABLE 13

| | EXAMPLE | | | | |
|---|---|---|---|---|---|
| | 24 | 25 | 26 | 27 | 28 |
| Component | Formulation (part by weight) | | | | |
| (A3) | (34) + As 0.80 | (36) + Gl 0.99 | (39) + Gl 0.99 | (42) + Gl 0.99 | (34) + Gl 1.00 |
| (B) | 126 + Gl 0.20 | 128 + Gl 0.01 | 133 + Gl 0.01 | 137 + Gl 0.01 | — |
| E1 | — | 3.00 | — | — | — |
| E2 | 3.00 | — | 3.00 | — | 3.00 |
| E3 | — | — | — | 3.00 | — |
| F1 | 2.00 | 2.00 | 2.00 | 1.00 | 2.00 |
| F2 | — | — | — | — | — |
| Emulsifier | 1.00 | 0.50 | 0.50 | 0.50 | 0.50 |
| Humectant | 3.00 | 3.00 | 3.00 | 3.00 | 3.00 |
| Low silicone | 1.00 | 2.00 | 3.00 | — | 2.00 |
| High silicone | — | — | — | 2.00 | — |
| G1 | — | — | 0.50 | 0.50 | 0.50 |
| G2 | 0.50 | 0.50 | — | — | — |
| H1 | 0.50 | 1.00 | — | — | — |
| H2 | — | — | 1.00 | 1.00 | 1.00 |
| Chelating agent | 0.10 | 0.10 | 0.10 | 0.10 | 0.10 |
| J1 | 1.00 | 1.50 | 2.00 | 2.00 | 2.00 |
| J2 | — | — | — | — | — |
| water | Added to make the whole 100 parts | | | | |
| Results of performance evaluation | | | | | |
| Skin irritation | 1 | 2 | 2 | 2 | 2 |
| Feel | 39 | 35 | 38 | 39 | 40 |
| Biodegradability | ⊚ | ⊚ | ⊚ | ⊚ | ⊚ |
| Thickening effect | ○ | ○ | ○ | ○ | ○~Δ |
| Emulsion stability | ○ | ○ | ○ | ○ | ○~Δ |

TABLE 14

| | COMPARATIVE EXAMPLE | | | |
|---|---|---|---|---|
| | 1 | 2 | 3 | 4 |
| Component | Formulation (part by weight) | | | |
| (A) | — | — | — | — |
| (B) | — | — | — | 125 + Gl 1.00 |
| Quaternary ammonium salt or tertiary amine salt of hydrochloric acid | C1 1.00 | C2 1.00 | C3 1.00 | — |
| E1 | — | — | — | — |
| E2 | 3.00 | 3.00 | 3.00 | 4.00 |
| E3 | — | — | — | — |
| F1 | — | — | 1.00 | — |
| F2 | 2.00 | 1.50 | — | 2.00 |
| Emulsifier | 1.00 | 1.00 | 1.00 | 1.0 |
| Humectant | 3.00 | 3.00 | 3.00 | 3.00 |
| Low silicone | 3.00 | 3.00 | 3.00 | 3.00 |
| High silicone | — | — | — | — |
| G1 | — | — | 0.50 | 0.50 |
| G2 | 0.50 | 0.50 | — | — |
| H1 | — | — | 0.50 | 0.50 |
| H2 | 0.50 | 0.50 | — | — |
| Chelating agent | 0.10 | 0.10 | 0.10 | 0.10 |
| J1 | 1.00 | — | 1.00 | — |
| J2 | — | 1.00 | — | 1.00 |
| water | Added to make the whole 100 | | | |
| Results of performance evaluation | | | | |
| Skin irritation | 35 | 30 | 2 | 8 |
| Feel | 20 | 20 | 18 | 15 |
| Biodegradability | x | x | Δ | Δ |
| Thickening effect | Δ | Δ | x | x |
| Emulsion stability | Δ | Δ | x | x |

In Tables 9 to 14, the quaternary ammonium amino acid salts (A1), (A2) and (A3) and the tertiary amine-neutralized amino acids (B) are each indicated by the combination of the quaternary ammonium (a1) in Table 1, quaternary ammonium (a2) in Table 2 or 3, or quaternary ammonium (a3) in Table 4 or 5, or tertiary amine (b) in Table 6, 7 or 8, and the amino acid.

In the tables, the proportions of the components are given on the pure effective component basis.

The additives used in Examples 1 to 28 and Comparative Examples 1 to 4 as shown in Tables 9 to 14 are as follows:

Higher Alcohol:
 E1: Cetyl alcohol
 E2: Stearyl alcohol
 E3: Behenyl alcohol
Fatty Acid Ester:
 F1: Octyl myristate
 F2: Cetyl 2-ethylhexanoate
Emulsifier: Glycerol monostearate
Humectant: Glycerol
Low silicone: Low-polymerization-degree dimethylpolysiloxane
High silicone: High-polymerization-degree dimethylpolysiloxane
Macromolecular Compound:
 G1: Cationized cellulose
 G2: Cationized guoir gum
Hydrocarbon Compound:
 H1: Solid paraffin
 H2: Liquid paraffin
Chelating agent: EDTA-2Na
Lower Alcohol:
 J1: Propylene glycol
 J2: Dipropylene glycol
Amino Acid:
 As: Aspartic acid
 G1: Glutamic acid The quaternary ammonium salts C1 to C3 used in Comparative Examples 1 to 3 are as follows:
 C1: Stearyltrimethylammonium chloride
 C2: Distearyldimethylammonium chloride
 C3: Behenyltrimethylammonium stearate Test Methods <Skin irritation>

From each of the compositions shown in Tables 9 to 14, a 1.0% aqueous surfactant solution was prepared and submitted to a closed patch test (48 hours, the ventral side of the upper arm) in 5 male and 5 female volunteers. The following evaluation criteria were used and the results were expressed in the sum of scores.

Evaluation Criteria

0: No reaction (erythema);

1: Slight erythema;

2: Definite erythema;

3: Moderate to intense erythema,

4: Beef-red erythema.

<Feel>

Four grams of each of the compositions shown in Tables 9 to 14 was taken and diluted with water to make 200 cc. A tuft of shampooed hair (15 cm long, weighing 5 g) was immersed therein at 40° C. for 5 seconds. Then, the hair was rinsed with two 200-cc portions of warm water at 40° C., over 30 seconds each, and then dried for 24 hours in the atmosphere controlled at 25° C. and 65% RH. After rinsing and after 24-hour drying, the tuft of hair was evaluated for flexibility, moist feel and smoothness by 10 panelists in terms of the sum of scores given according to the following scoring criteria.

Scoring Criteria

0: Inferior to the standard rinse;

1: Rather inferior to the standard rinse;

2: Comparable to the standard rinse;

3: Rather superior to the standard rinse;

4: Superior to the standard rinse.

The composition of Comparative Example 1 was used as the standard rinse.

<Biodegradability>

From each of the compositions shown in Tables 9 to 14, a 40 ppm aqueous surfactant solution was prepared and submitted to biodegradability testing according to the OECD Guidelines for Testing Chemicals: 301A, Die-Away test method. The following evaluation criteria were employed.

Evaluation Criteria

⊚: Very good biodegradability as compared with the standard surfactant;

○: Good biodegradability as compared with the standard surfactant;

Δ: Comparable in biodegradability to the standard surfactant;

X: Inferior in biodegradability to the standard surfactant.

The composition of Comparative Example 3 was used as the standard surfactant.

<Thickening effect>

The compositions shown in Tables 9 to 14 were checked for thickening effect.

○: Highly satisfactory viscosity as a rinse;

Δ: Fairly satisfactory viscosity as a rinse;

X: Unsatisfactory viscosity as a rinse.

<Emulsion stability>

The compositions shown in Tables 9 to 14 were checked for emulsions stables at ertandine at 50° C. for 30 days.

○: No separation;

Δ: Partial separation;

X: Complete separation.

From Tables 9 to 14, it is apparent that the quaternary ammonium amino acid salts (A1), (A2) and (A3) and mixtures of these with the tertiary amine-neutralized amino acids (B), all provided by the present invention, are satisfactory in terms of dermal or other irritation potential, ability to provide hair with good feel, and biodegradability. Furthermore, they are excellent in thickening effect and emulsion stability as well.

The quaternary ammonium amino acid salts of the present invention provide good posttreatment feel of hair, typically smooth flow and moist feel of hair, and show good biodegradability and low skin irritation and therefore are useful as environment- and human-friendly hair treatment agents. They are also excellent in thickening effect and emulsion stability. Thus, they are very useful as hair treatment agents.

What is claimed is:

1. A hair treatment composition which comprises an aqueous solution or an aqueous dispersion of at least one quaternary ammonium salt (A) represented by the general formula (I), (2) or (3):

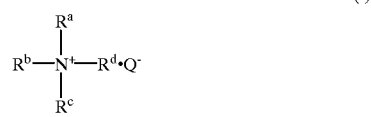

(I)

wherein $R^a$ represents an organic group containing 6 to 32 carbon atoms, $R^b$ and $R^c$ are the same or different and each represents an organic group containing 1 to 32 carbon atoms, $R^d$ represents an organic group containing 1 to 4 carbon atoms, and $Q^-$ represents an amino acid anion;

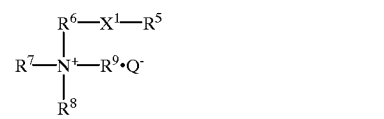

(2)

wherein $X^1$ represents an ester group;

$R^5$ represents an alkyl, alkenyl or hydroxyalkyl group and $R^6$ represents an alkylene, alkenylene or hydroxyalkylene group, the sum of carbon atoms contained in $R^5$ and $R^6$ being 6 to 32, $R^7$ and $R^8$ are the same or different and each represents a group of the formula $R^5$—$X^1$—$R^6$—, an alkyl group containing 1 to 4 carbon atoms or a hydroxyalkyl group containing 2 to 4 carbon atoms, $R^9$ represents an alkyl group containing 1 to 4 carbon atoms or a hydroxyalkyl group containing 2 to 4 carbon astoms, and $Q^-$ represents an amino acid anion;

wherein said amino acid in formula (2) is selected from the group from the group consisting of glycine, alanine, valine, leucine, isoleucine, serine, threonine, cystine, methionine, asparagine, glutamine, phenylalanine, tyrsine, proline, tryptophan, aspartic acid, glutamic acid, cysteic acid, lysine, arginine and histidine;

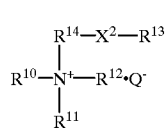
(3)

wherein
- $X^2$ represents an amide group,
- $R^{13}$ represents an alkyl, alkenyl or hydroxyalkyl group and $R^{14}$ represents an alkylene, alkenylene or hydroxyalkylene group, the sum of carbon atoms contained in $R^{13}$ and $R^{14}$ being 6 to 32,
- $R^{10}$ and $R^{11}$ are the same or different and each represents a group of the formula $R^{13}$—$X^2$—$R^{14}$—, a group of the formula $R^5$—$X^1$—$R^6$—, an alkyl group containing 1 to 4 carbon atoms or a hydroxyalkyl group containing 2 to 4 carbon atoms,
- $X^1$ represents an ester group, $R^5$ represents an alkyl, alkenyl or hydroxyalkyl group and $R^6$ represents an lakylene, alkenylene or hydroxyalkylene group, the sum of carbon atoms contained in $R^5$ and $R^6$ being 6 to 32,
- $R^{12}$ represents an alkyl group containing 1 to 4 carbon atoms or a hydroxyalkyl group containing 2 to 4 carbon atoms, and
- $Q^-$ represents an amino acid anion.

2. The hair treatment composition according to claim 1, wherein said salt (A) is a quaternary ammonium salt (A1) represented by the general formula (1):

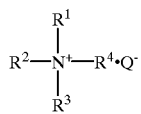
(1)

wherein
- $R^1$ represents an alkyl group containing 6 to 28 carbon atoms, an alkenyl group containing 6 to 28 carbon atoms or a hydroxyalkyl group containing 6 to 28 carbon atoms,
- $R^2$ and $R^3$ are the same or different and each represents an alkyl group containing 1 to 28 carbon atoms, an alkenyl group containing 2 to 28 carbon atoms or a hydroxyalkyl group containing 2 to 28 carbon atoms,
- $R^4$ represents an alkyl group containing 1 to 4 carbon atoms or a hydroxyalkyl group containing 2 to 4 carbon atoms, and
- $Q^-$ represents an amino acid anion.

3. The hair treatment composition according to claim 2, wherein
- $R^1$ is an alkyl group containing 12 to 24 carbon atoms, an alkenyl group containing 12 to 24 carbon atoms or a hydroxyalkyl group containing 12 to 24 carbon atoms and $R^2$ and $R^3$ are the same or different and each is an alkyl group containing 1 to 4 carbon atoms or a hydroxyalkyl group containing 2 to 4 carbon atoms.

4. The hair treatment composition according to claim 1, wherein said salt (A) is a quaternary ammonium salt (A2) represented by the general formula (2):

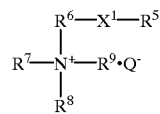
(2)

wherein
- $X^1$ represents an ester group,
- $R^5$ represents an alkyl, alkenyl or hydroxyalkyl group and $R^6$ represents an alkylerie, alkenylene or hydroxyalkylene group, the sum of carbon atoms contained in $R^5$ and $R^6$ being 6 to 32,
- $R^7$ and $R^8$ are the same or different and each represents a group of the formula $R^5$—$X^1$—$R^6$—, an alkyl group containing 1 to 4 carbon atoms or a hydroxyalkyl group containing 2 to 4 carbon atoms,
- $R^9$ represents an alkyl group containing 1 to 4 carbon atoms or a hydroxyalkyl group containing 2 to 4 carbon atoms, and
- $Q^-$ represents an amino acid anion.

5. The hair treatment composition according to claim 4, wherein $R^7$ and $R^8$ are the same or different and each is an alkyl group containing 1 to 4 carbon atoms or a hydroxyalkyl group containing 2 to 4 carbon atoms.

6. The hair treatment composition according to claim 1, wherein said salt (A) is a quaternary ammonium salt (A3) represented by the general formula (3):

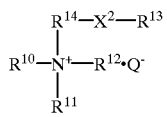
(3)

wherein
- $X^2$ represents an amide group,
- $R^{13}$ represents an alkyl, alkenyl or hydroxyalkyl group and $R^{14}$ represents an alkylene, alkenylene or hydroxyalkylene group, the sum of carbon atoms contained in $R^{13}$ and $R^{14}$ being 6 to 32,
- $R^{10}$ and $R^{11}$ are the same or different and each represents a group of the formula $R^{13}$—$X^2$—$R^{14}$—, a group of the formula $R^5$—$X^1$—$R^6$—, an alkyl group containing 1 to 4 carbon atoms or a hydroxyalkyl group containing 2 to 4 carbon atoms,
- $X^1$ represents an ester group, $R^5$ represents an alkyl, alkenyl or hydroxyalkyl group and $R^6$ represents an alkylene, alkenylene or hydroxyalkylene group, the sum of carbon atoms contained in $R^5$ and $R^6$ being 6 to 32,
- $R^{12}$ represents an alkyl group containing 1 to 4 carbon atoms or a hydroxyalkyl group containing 2 to 4 carbon atoms, and
- $Q^-$ represents an amino acid anion.

7. The hair treatment composition according to claim 6, wherein $R^{10}$ and $R^{11}$ are the same or different and each is an alkyl group containing 1 to 4 carbon atoms or a hydroxyalkyl group containing 2 to 4 carbon atoms.

8. The hair treatment composition according to claim 1, wherein the amino acid of formula I or II is at least one selected from the group consisting of glycine, alanine, valine, leucine, isoleucine, serine, threonine, cysteine, methionine, asparagine, glutamine, phenylalanine, tyrosine, proline, tryptophan, aspartic acid, glutamic acid, cysteic acid, lysine, arginine and histidine.

9. The hair treatment composition according to claim 1, wherein the amino acid is aspartic acid or glutamic acid.

10. A hair treatment composition according to claim 1 which further comprises at least one tertiary amine salt (B) represented by the general formula (4):

(4)

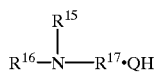

wherein
- $R^{15}$ represents an alkyl group containing 6 to 28 carbon atoms, an alkenyl group containing 6 to 28 carbon atoms, a hydroxyalkyl group containing 6 to 28 carbon atoms, a group of the formula $R^5-X^1-R^6-$ or a group of the formula $R^{13}-X^2-R^{14}-$,
- $R^{16}$ and $R^{17}$ are the same or different and each represents an alkyl group containing 1 to 28 carbon atoms, an alkenyl group containing 2 to 28 carbon atoms, a hydroxyalkyl group containing 2 to 28 carbon atoms, a group of the formula $R^5-X^1-R^6-$ or a group of the formula $R^{13}-X^2-R^{14}-$,
  - $X^1$ represents an ester group, $R^5$ represents an alkyl, alkenyl or hydroxyalkyl group and $R^6$ represents an alkylene, alkenylene or hydroxyalkylene group, the sum of carbon atoms contained in $R^5$ and $R^6$ being 6 to 32,
  - $X^2$ represents an amide group, $R^{13}$ represents an alkyl, alkenyl or hydroxyalkyl group and $R^{14}$ represents an alkylene, alkenylene or hydroxyalkylene group, the sum of carbon atoms contained in $R^{13}$ and $R^{14}$ being 6 to 32, and
- QH represents an amino acid.

11. The hair treatment composition according to claim 10, wherein the weight ratio (A)/(B) is 99.9/0.1 to 50/50.

12. The hair treatment composition according to claim 1, wherein the concentration of (A) is 0.1 to 30% by weight, based on the hair treatment composition.

13. The hair treatment composition according to claim 10, wherein the concentration of (A) plus (B) is 0.1 to 30% by weight, based on the hair treatment composition.

14. A hair rinse conditioner or treatment composition comprising 0.5 to 20% by weight of a cationic surfactant comprising said quaternary ammonium salt (A) of claim 1, or (A) and said tertiary amine salt (B) represented by the general formula (4):

(4)

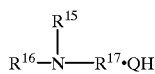

wherein
- $R^{15}$ represents an alkyl group containing 6 to 28 carbon atoms, an alkenyl group containing 6 to 28 carbon atoms, a hydroxyalkyl group containing 6 to 28 carbon atoms, a group of the formula $R^5-X^1-R^6-$ or a group of the formula $R^{13}-X^2-R^{14}-$,
- $R^{16}$ and $R^{17}$ are the same or different and each represents an alkyl group containing 1 to 28 carbon atoms, an alkenyl group containing 2 to 28 carbon atoms, a hydroxyalkyl group containing 2 to 28 carbon atoms, a group of the formula $R^5-X^1-R^6-$ or a group of the formula $R^{13}-X^2-R^{14}-$,
  - $X^1$ represents an ester group, $R^5$ represents an alkyl, alkenyl or hydroxyalkyl group and $R^6$ represents an alkylene, alkenylene or hydroxyalkylene group, the sum of carbon atoms contained in $R^5$ and $R^6$ being 6 to 32,
  - $X^2$ represents an amide group, $R^{13}$ represents an alkyl, alkenyl or hydroxylakyl group and $R^{14}$ represents an alkylene, alkenylene or hydroxyalkylene group, the sum of carbon atoms contained in $R^{13}$ and $R^{14}$ being 6 to 32, and
- QH represents an amino acid,
0 to 5% by weight of a humectant, 0 to 10% by weight of an additive selected from the group consisting of chelating agents, lawer alcohols, macromolecular compounds, perfumes, colorants, preservatives and ultraviolet absorbers, and 25 to 99% by weight of water.

15. The hair rinse, conditioner or treatment composition according to claim 14, wherein the macromolecular compound is at least one selected from the group consisting of cationized cellulose, cationized guar gum, polyethylene glycol, polypropylene glycol, sodium polyacrylate, hydroxyethylcellulose, protein derivatives and (N-methacryloyloxyethyl-N,N-dimethylammonium-α-N-methylcarboxybetaine)-(alkylmethacrylate) copolymers.

16. A shampoo composition comprising 0.5 to 10% by weight of a cationic surfactant comprising said quaternary ammonium salt (A) of claim 1, or (A) and said tertiary amine salt (B) represented by the general formula (4):

(4)

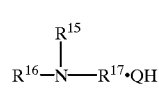

wherein
- $R^{15}$ represents an alkyl group containing 6 to 28 carbon atoms, an alkenyl group containing 6 to 28 carbon atoms, a hydroxylakyl group containing 6 to 28 carbon atoms, a group of the formula $R^5-X^1-R^6-$ or a group of the formula $R^{13}-X^2-R^{14}-$,
- $R^{16}$ and $R^{17}$ are the same or different and each represents an alkyl group containing 1 to 28 carbon atoms, an alkenyl group containing 2 to 28 carbon atoms, a hydroxyalkyl group containing 2 to 28 carbon atoms, a group of the formula $R^5-X^1-R^6-$ or a group of the formula $R^{13}-X^2-R^{14}-$,
  - $X^1$ represents an ester group, $R^5$ represents an alkyl, alkenyl or hydroxyalkyl group and $R^6$ represents an alkylene, alkenylene or hydroxyalkylene group, the sum of carbon atoms contained in $R^5$ and $R^6$ being 6 to 32,
  - $X^2$ represents an amide group, $R^{13}$ represents an alkyl, alkenyl or hydroxylakyl group and $R^{14}$ represents an alkylene, alkenylene or hydroxyalkylene group, the sum of carbon atoms contained in $R^{13}$ and $R^{14}$ being 6 to 32, and
- QH represents an amino acid,
1.0 to 30% by weight of an anionic surfactant, 0 to 10% by weight of an amphoteric surfactant, 0.5 to 10% by weight of an nonionic surfactant, 0 to 10% by weight of a humectant, 0 to 5% by weight of an additive selected from the group consisting of chelating agents, macromolecular compounds, perfumes, colorants, preservatives and ultraviolet absorbers, and 25 to 98% by weight of water.

17. The shampoo composition according to claim 16, wherein the macromolecular compound is at least one selected from the group consisting of cationized cellulose, cationized guar gum, polyethylene glycol, polypropylene glycol, sodium polyacrylate, hydroxyethylcellulose, protein derivatives and (N-methacryloyloxyethyl-N,N-dimethylammonium-α-N-methylcarboxybetaine)-(alkylmethacrylate) copolymers.

18. A hair dye composition comprising 0.1 to 5% by weight of a cationic surfactant comprising said quaternary ammonium salt (A) of claim 1, or (A) and said tertiary amine salt (B) represented by the general formula (4):

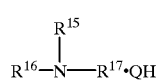
(4)

wherein $R^{15}$ represents an alkyl group containing 6 to 28 carbon atoms, an alkenyl group containing 6 to 28 carbon atoms, a hydroxylakyl group containing 6 to 28 carbon atoms, a group of the formula $R^5$—$X^1$—$R^6$— or a group of the formula $R^{13}$—$X^2$—$R^{14}$—, $R^{16}$ and $R^{17}$ are the same or different and each represents an alkyl group containing 1 to 28 carbon atoms, an alkenyl group containing 2 to 28 carbon atoms, a hydroxyalkyl group containing 2 to 28 carbon atoms, a group of the formula $R^5$—$X^1$—$R^6$— or a group of the formula $R^{13}$—$X^2$—$R^{14}$—, $X^1$ represents an ester group, $R^5$ represents an alkyl, alkenyl or hydroxyalkyl group and $R^6$ represents an alkylene, alkenylene or hydroxyalkylene group, the sum of carbon atoms contained in $R^5$ and $R^6$ being 6 to 32, $X^2$ represents an amide group, $R^{13}$ represents an alkyl, alkenyl or hydroxylakyl group and $R^{14}$ represents an alkylene, alkenylene or hydroxyalkylene group, the sum of carbon atoms contained in $R^{13}$ and $R^{14}$ being 6 to 32, and QH represents an amino acid, 0.5 to 10% by weight of an acid dye, 1 to 30% by weight of a solvent, 0 to 5% by weight of a pH adjusting agent, 0 to 5% by weight of a thickener and 45 to 98.4% by weight of water.

19. A hair setting composition comprising 0.1 to 10% by weight of a cationic surfactant comprising said quaternary ammonium salt (A) of claim 1, or (A) and said tertiary amine salt (B) represented by the general formula (4):

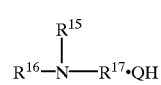
(4)

wherein $R^{15}$ represents an alkyl group containing 6 to 28 carbon atoms, an alkenyl group containing 6 to 28 carbon atoms, a hydroxylakyl group containing 6 to 28 carbon atoms, a group of the formula $R^5$—$X^1$—$R^6$— or a group of the formula $R^{13}$—$X^2$—$R^{14}$—, $R^{16}$ and $R^{17}$ are the same or different and each represents an alkyl group containing 1 to 28 carbon atoms, an alkenyl group containing 2 to 28 carbon atoms, a hydroxyalkyl group containing 2 to 28 carbon atoms, a group of the formula $R^5$—$X^1$—$R^6$— or a group of the formula $R^{13}$—$X^2$—$R^{14}$—, $X^1$ represents an ester group, $R^5$ represents an alkyl, alkenyl or hydroxyalkyl group and $R^6$ represents an alkylene, alkenylene or hydroxyalkylene group, the sum of carbon atoms contained in $R^5$ and $R^6$ being 6 to 32, $X^2$ represents an amide group, $R^{13}$ represents an alkyl, alkenyl or hydroxylakyl group and $R^{14}$ represents an alkylene, alkenylene or hydroxyalkylene group, the sum of carbon atoms contained in $R^{13}$ and $R^{14}$ being 6 to 32, and QH represents an amino acid, 0.5 to 20% by weight of a macromolecular compound, 0.5 to 10% by weight of an oil, 0 to 5% by weight of a humectant, 0 to 5% by weight of a chelating agent, 0.5 to 30% by weight of a lower alcohol, 0 to 5% by weight of a nonionic surfactant, 0 to 5% by weight of an additive selected from the group consisting of perfumes, colorants, preservatives and ultraviolet absorbers, and 15 to 98.4% by weight of water.

20. The hair setting composition according to claim 19, wherein the macromolecular compound is at least one selected from the group consisting of cationized cellulose, cationized guar gum, polyethylene glycol, polypropylene glycol, sodium polyacrylate, hydroxyethylcellulose, protein derivatives, (N-methacryloyloxyethyl-N,N-dimethylammonium-α-N-methylcarboxybetaine)-(alkylmethacrylate) copolymers, acrylic resin-alkanolamines, carboxyvinyl polymers, and polyvinylpyrrolidone-vinyl acetate copolymers.

* * * * *